United States Patent
Ozawa et al.

(10) Patent No.: US 8,546,129 B2
(45) Date of Patent: Oct. 1, 2013

(54) SAMPLE ANALYSIS CHIP, SAMPLE ANALYZER USING SAMPLE ANALYSIS CHIP, SAMPLE ANALYSIS METHOD, AND METHOD OF PRODUCING SAMPLE ANALYSIS CHIP

(75) Inventors: Tomoyuki Ozawa, Tokyo (JP); Nao Nishijima, Kasukabe (JP); Ming Yin, Kasukabe (JP)

(73) Assignee: Toppan Printing Co., Ltd., Tokyo (JP)

( * ) Notice: Subject to any disclaimer, the term of this patent is extended or adjusted under 35 U.S.C. 154(b) by 0 days.

(21) Appl. No.: 13/138,756

(22) PCT Filed: Mar. 30, 2010

(86) PCT No.: PCT/JP2010/055721
§ 371 (c)(1),
(2), (4) Date: Sep. 23, 2011

(87) PCT Pub. No.: WO2010/113959
PCT Pub. Date: Oct. 7, 2010

(65) Prior Publication Data
US 2012/0015828 A1     Jan. 19, 2012

(30) Foreign Application Priority Data

Mar. 31, 2009 (JP) ................................. 2009-085272
Mar. 31, 2009 (JP) ................................. 2009-085273
Mar. 31, 2009 (JP) ................................. 2009-085274

(51) Int. Cl.
*C12M 1/00* (2006.01)
*C12M 1/34* (2006.01)
*C12M 3/00* (2006.01)
*G01N 15/06* (2006.01)
*G01N 33/00* (2006.01)
*G01N 33/48* (2006.01)
*C40B 10/00* (2006.01)
*C12Q 1/68* (2006.01)

(52) U.S. Cl.
USPC ..... 435/283.1; 435/6.1; 435/288.5; 422/68.1; 506/9

(58) Field of Classification Search
USPC ................... 435/6.1, 283.1, 288.5; 422/68.1; 506/9
See application file for complete search history.

(56) References Cited

U.S. PATENT DOCUMENTS 5,246,666 A * 9/1993 Vogler et al. ..................... 422/73
5,631,166 A * 5/1997 Jewell ............................. 436/45

(Continued)

FOREIGN PATENT DOCUMENTS

CN    1638871 A    7/2005
CN    1829569 A    9/2006

(Continued)

OTHER PUBLICATIONS

International Search Report mailed on Jun. 29, 2010 in corresponding PCT Application No. PCT/JP2010/055721.

(Continued)

*Primary Examiner* — Narayan Bhat

(57) ABSTRACT

A low cost sample analysis chip in which liquid is supplied to wells formed on the chip so as to carry out reaction by a simple liquid supply method with no variation in the amount of liquid in each well, the sample analysis chip including a plurality of wells and a flow passage leading to the respective wells, wherein the flow passage includes a main flow passage which supplies liquid to each well, and the sample analysis chip has the main flow passage provided closer to the rotation center side than the well; and is formed so as to have one peak between neighboring wells in the direction of rotation center.

31 Claims, 8 Drawing Sheets

(56) References Cited

U.S. PATENT DOCUMENTS

| | | | |
|---|---|---|---|
| 7,692,794 B2 * | 4/2010 | Kim et al. | 356/418 |
| 2002/0047003 A1 * | 4/2002 | Bedingham et al. | 219/388 |
| 2006/0252144 A1 * | 11/2006 | Sandell | 435/288.5 |

FOREIGN PATENT DOCUMENTS

| | | |
|---|---|---|
| JP | 60-154160 | 8/1985 |
| JP | 2001-526778 | 12/2001 |
| JP | 2004-502164 | 1/2004 |
| JP | 2004-529333 | 9/2004 |
| JP | 2005-518531 | 6/2005 |
| JP | 3699721 | 9/2005 |
| JP | 2007-33226 | 2/2007 |
| JP | 2007-527517 | 9/2007 |
| JP | 2008-083017 | 4/2008 |
| JP | 3142125 | 5/2008 |
| JP | 4181046 | 11/2008 |
| WO | 98/43739 | 10/1998 |
| WO | 02/01180 | 1/2002 |
| WO | 02/074438 | 9/2002 |
| WO | 03/057369 | 7/2003 |
| WO | 2006/137431 A1 | 12/2006 |

OTHER PUBLICATIONS

Japanese Office Action mailed Nov. 29, 2011 issued in corresponding Japanese Patent Application No. 2011-507222.
Chinese Office Action mailed Jun. 5, 2013 in Chinese Application No. 201080014320.2.

* cited by examiner

FIG. 5A
FIG. 5B
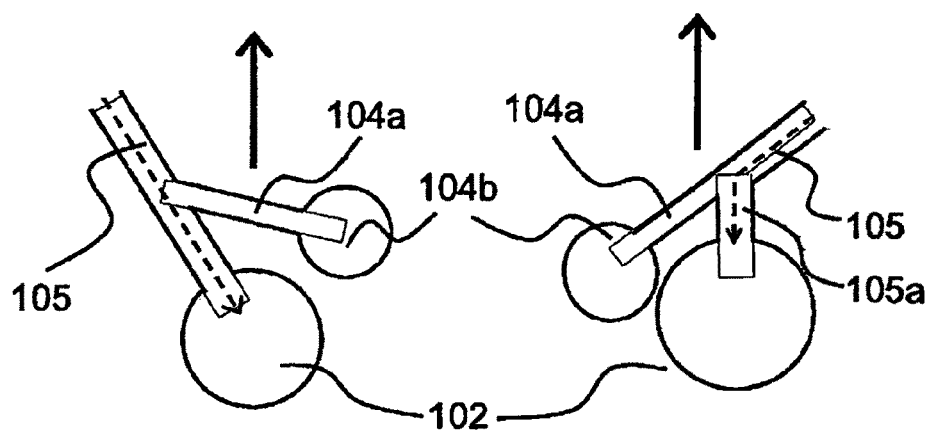
FIG. 6
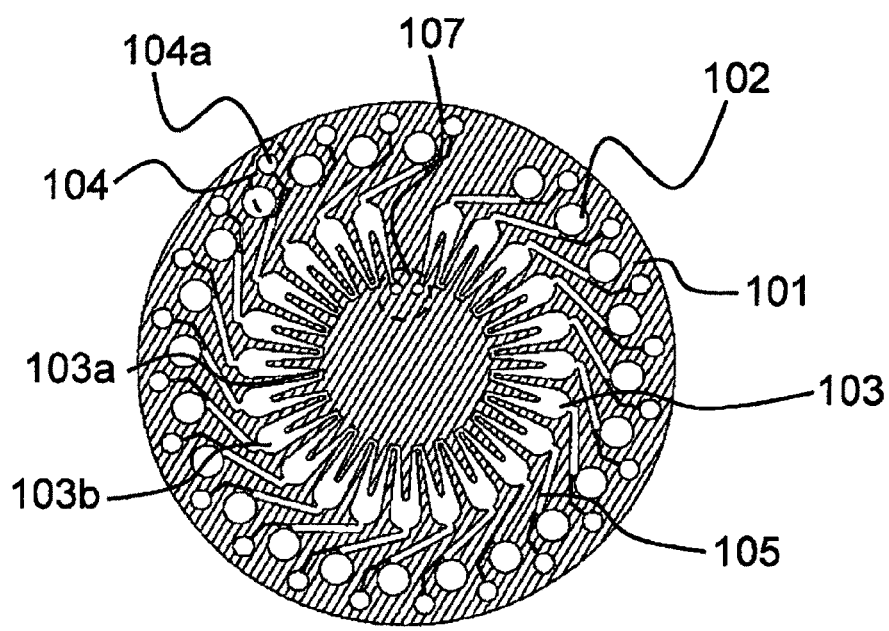

FIG. 11A
FIG. 11B
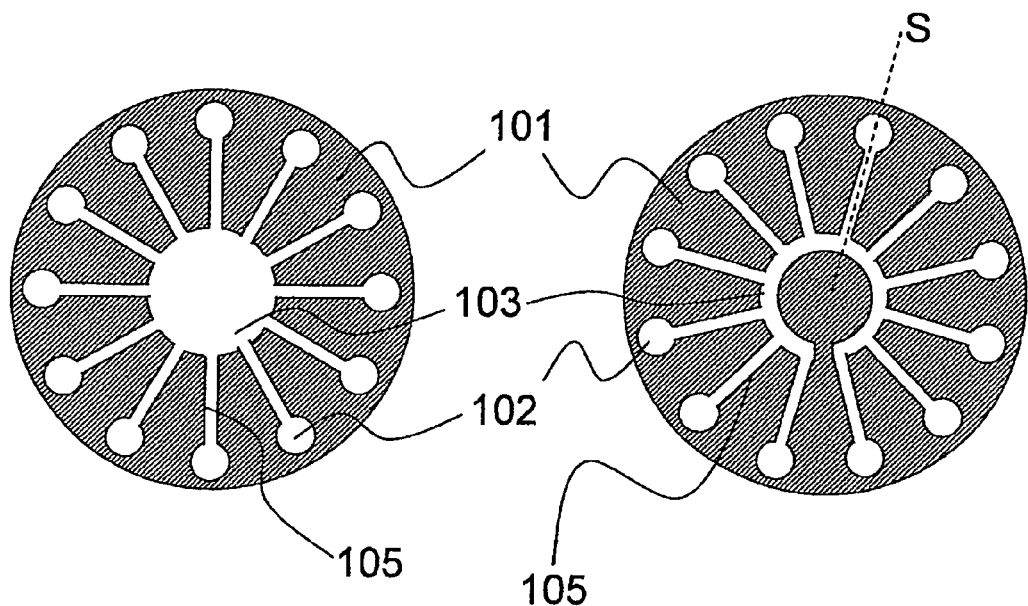
FIG. 12
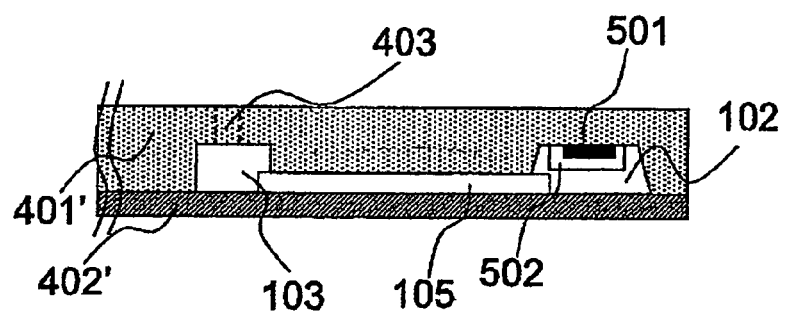

SAMPLE ANALYSIS CHIP, SAMPLE ANALYZER USING SAMPLE ANALYSIS CHIP, SAMPLE ANALYSIS METHOD, AND METHOD OF PRODUCING SAMPLE ANALYSIS CHIP

CROSS-REFERENCE TO RELATED APPLICATIONS

This is a U.S. National Phase Application under 35 U.S.C. §371 of International Patent Application No. PCT/JP2010/055721 filed Mar. 30, 2010, which claims the benefit of Japanese Patent Application No. 2009-085272, filed Mar. 31, 2009, Japanese Patent Application No. 2009-085273, filed Mar. 31, 2009, and Japanese Patent Application No. 2009-085274, filed Mar. 31, 2009, all of which are hereby incorporated by reference.

Priority is claimed on Japanese Patent Application No. 2009-085272, Japanese Patent Application No. 2009-085273 and Japanese Patent Application No. 2009-085274, filed Mar. 31, 2009, the contents of which are incorporated herein by reference.

TECHNICAL FIELD

The present invention relates to a sample analysis chip and a sample analysis method that are used in the detection and analysis of biochemical reactions or the like, and also to a method of producing a sample analysis chip. The present invention particularly relates to a disposable chip that can be used in the DNA analysis and to a production method thereof.

BACKGROUND ART

In the field of biochemical reactions such as DNA reactions and protein reactions, techniques called μ-TAS (Total Analysis System) and Lab-on-Chip have been conventionally known in a reactor for treating a trace amount of sample solution. In these techniques, a plurality of reaction chambers (hereafter, referred to as wells) and flow passages are provided in a single chip or a cartridge. Thus, analysis of a plurality of specimens and a plurality of reactions can be carried out. These techniques have various advantages since the amount of chemicals to be handled can be reduced through miniaturization of the chip or the cartridge.

Examples of such advantages include: a reduction in the amount of conventionally used chemicals, such as strong acid and strong alkali, thereby dramatically reducing the impact on the human body and on the environment; and also a reduction in the consumption of expensive reagents used in the biochemical reaction or the like, thereby reducing the cost required for the analysis and reaction.

In order to carry out a biochemical reaction most efficiently using a chip or a cartridge, it is necessary that different types of chemicals, samples and enzymes are each disposed in a plurality of wells, and then, reagents for causing the reaction with these chemicals, samples and enzymes are collectively introduced into the wells through a single or a plurality of main conduits, thereby allowing a plurality of different reactions to proceed.

By using this technique, multiple types of specimens can be treated with the same reagent at the same time, or one type of specimen can be subjected to a plurality of treatments at the same time. As a result, it becomes possible to considerably reduce the time and labor required in the prior art.

When employing this kind of technique, a technique for supplying an equal amount of samples to a plurality of reaction fields and also a technique for preventing mixing of the contents in each well become important. Examples of the prior arts regarding such chips for supplying liquid samples to the wells include the following.

In Patent Document 1, in a chip that supplies liquid samples from a liquid reservoir to the wells by centrifugal force, flow channels are deformed and sealed so as to separate the wells. For this reason, a mechanism to crush the flow channels is required, making the automation difficult. In addition, if the liquid samples are supplied from the central liquid reservoir to the surrounding wells by centrifugal force as in the conventional centrifugally supplying chips, the amount of liquid samples supplied to each well varies.

In Patent Document 2, the problem of variations in the amount of liquid samples supplied to each well is solved by employing a centrifugal method that combines rotation and revolution. However, this technique also requires a complicated mechanism and space for rotating/revolving chips.

In Patent Document 3, a medium for analysis in which a liquid reservoir section and a plurality of wells having a flow channel extended in the centrifugal direction are connected has been disclosed. However, this document pays no attention to the delivery of liquids, but describes a fluid control through the pressing of air filled in the wells. In this technique, the result differs from reaction to reaction because not only the liquid in the channel between the two liquid reservoir sections is not supplied but also the amount of liquid supplied to each well varies greatly.

Therefore, the first problem associated with the prior art is the unavailability of chips employing a simple liquid supply method while reducing variations in the amount of liquid in each well.

In addition, as the second problem associated with these techniques, since it is necessary to deliver the sample material to a plurality of wells within an instrument, cross contamination may occur among the chambers, which leads to wrong test results.

As a technique for solving the above-mentioned problems, a sealed-type chip has been proposed, which is formed by pasting two members together, while at least one of the members has been processed and provided with a flow passage or the like. For example, in Patent Document 1, a sealed-type process array and a sample processing apparatus have been disclosed, that are constituted of a first principal surface member providing a structure that includes a loading chamber, a main conduit and a process chamber (well), and a second principal surface member, in which the process chamber is arranged alongside the conduit that extends from the loading chamber, and the loading chamber, the conduit and the process chamber are aligned alongside the longitudinal direction of the sample processing apparatus.

The process array described in Patent Document 4 is provided with a plurality of process chambers connected via feed conduits that are branched from one main conduit. For this reason, operations such as those to treat a plurality types of specimens with the same reagent are possible. In order to carry out biochemical reactions in the most efficient manner by using these process arrays, different kinds of chemicals, specimens and enzymes are first disposed in a plurality of reaction fields. Then the reagent that reacts with them is poured into the respective reaction fields from a single or a plurality of main conduits. It is necessary to cause several different reactions as described above. By employing this technique, multiple types of specimens can be treated with the same reagent at the same time, or one type of specimen can be subjected to a plurality of treatments at the same time. As a result, it becomes possible to considerably reduce the time and labor required in the prior art.

As this type of technique, for example, by employing a microfluid chip equipped with a liquid inlet, a flow passage, a liquid outlet and the like, a technique has been disclosed, in which a portion of reagent components required for the reaction is fixed within the chip flow passage in a solid state through a process such as freeze drying, the remaining portion of reagent components required for the reaction is supplied in a liquid state, and the reaction is allowed to proceed by bringing these components into contact within the flow passage.

In addition, Patent Document 5 discloses a sample processing apparatus formed by pasting together a resin substrate having a loading chamber, a process chamber and a flow passage formed therein, and a flat metal substrate. Further, when allowing different reactions to proceed in each process chamber, a method for blocking the flow passage so that each process chamber becomes an enclosed space has been disclosed. In this sample processing apparatus, the flat metal substrate is deformed so as to be forced into the flow passage, thereby blocking the flow passage.

However, a pressure sensitive adhesive is used between the first principal surface member and the second principal surface member in the process array described in Patent Document 1. The use of a pressure sensitive adhesive causes elution from the adhesive during reaction, which may adversely affect the reagent inside the well. In addition, problems of heat resistance or water resistance associated with the adhesive layer readily occurs, and the constitution described in Patent Document 1 is inadequate for sealing the flow passage in order to avoid the effects from the outside.

Moreover, it is extremely important to precisely control the reaction temperature or temperature cycling conditions when conducting biochemical reactions or the like. The metal substrate side is made into a flat plate shape in the sample processing apparatus described in Patent Document 2. It has been described that, for this reason, adhesion with the heating blocks or the like improves, which makes it suitable for the reactions involving thermal cycles. However, it is necessary to block the flow passage to form each process chamber into an enclosed space when carrying out reactions using the sample processing apparatus described in Patent Document 2. In this sample processing apparatus, the flat metal substrate is deformed so as to be forced into the flow passage, thereby blocking the flow passage. Due to deformation of the metal substrate as described above, the flatness of the metal substrate is impaired, the adhesion with the heating blocks reduces, and the thermal responsiveness becomes inadequate, which makes it difficult to carry out desired reactions reliably and within a short space of time. Moreover, in the method described in Patent Document 2, when the blocking of the flow passage is inadequate, cross contamination may occur among the chambers which leads to wrong test results.

[Citation List]

[Patent Documents]

[Patent Document 1] Published Japanese Translation No. 2004-502164 of the PCT International Publication

[Patent Document 2] Japanese Patent Publication No. 3699721

[Patent Document 3] Japanese Unexamined Patent Application, First Publication No. 2008-83017

[Patent Document 4] Japanese Patent Publication No. 4181046

[Patent Document 5] Published Japanese Translation No. 2004-502164 of the PCT International Publication

SUMMARY OF INVENTION

[Technical Problem]

In view of the problems associated with the prior art as described above, the present invention has an object of providing a low cost sample analysis chip for supplying a liquid to wells, which employs a simple liquid supply method while reducing variations in the amount of liquid in each well.

Further, another object is to provide a sample analysis chip which can be easily prepared while is free from sample contamination or the like within the wells formed on the chip, and the production method thereof.

[Solution to Problem]

[1] An invention of the present invention which is made in order to solve the problems as described above is a sample analysis chip having, on a base material, a plurality of wells, a flow passage leading to the respective wells, and an injection port for injecting a solution into the flow passage, and delivers the solution to wells by rotating the base material, and the sample analysis chip is characterized in that the flow passage includes a main flow passage which supplies liquid to the respective wells, and the main flow passage is provided closer to the rotation center side than to the wells, and is formed so as to have one peak between neighboring wells in the direction of rotation center.

[2] An invention is the sample analysis chip described in [1] characterized in that the aforementioned well and the main flow passage are connected in a valley portion between the peaks of the main flow passage.

[3] An invention is the sample analysis chip described in [1] or [2] characterized in that a passage width of the aforementioned main flow passage is relatively small in a peak portion and large in a valley portion.

[4] An invention is the sample analysis chip described in any one of [1] to [3] characterized in that the aforementioned base material has a disc shape and the aforementioned wells are arranged concentrically to the base material.

[5] An invention is the sample analysis chip described in any one of [1] to [4] characterized by having a side passage that connects the aforementioned main flow passage and the aforementioned well.

[6] An invention is the sample analysis chip described in [5] characterized in that the aforementioned side passage is formed so as to be inclined with respect to the direction of rotation center.

[7] An invention is the sample analysis chip described in any one of [1] to [6] characterized in that the aforementioned main flow passage is formed so as to be inclined with respect to the direction of rotation center.

[8] An invention is the sample analysis chip described in any one of [1] to [7] characterized by further having a side passage that connects the aforementioned main flow passage and the aforementioned well, and a waste solution portion provided in the aforementioned side passage for storing a residual solution.

[9] An invention is the sample analysis chip described in [8] characterized in that the aforementioned waste solution portion includes a waste solution chamber for storing a waste solution, and a waste solution chamber branch flow passage that is branched from the aforementioned side passage and connected to the waste solution chamber.

[10] An invention is the sample analysis chip described in [8] or [9] characterized in that the aforementioned side passage is formed so as to be inclined with respect to the direction of rotation center, and the aforementioned waste solution portion is provided on the inner side of the side passage with respect to the direction of rotation center.

[11] An invention is the sample analysis chip described in [9] or [10] characterized in that the branch flow passage connected to the aforementioned wells has a lower pressure loss during the supply of liquids than the branch flow passage connected to the aforementioned waste solution chamber.

[12] An invention is the sample analysis chip described in [11] characterized in that a cross sectional area of the branch flow passage connected to the aforementioned wells is larger than a cross sectional area of the waste solution chamber branch flow passage.

[13] An invention is the sample analysis chip described in [11] characterized in that the branch flow passage connected to the aforementioned well has a lower surface roughness than the waste solution chamber branch flow passage.

[14] An invention is the sample analysis chip described in [11] characterized in that an inner surface of the waste solution chamber branch flow passage is subjected to a water repellency treatment.

[15] An invention is the sample analysis chip described in [11] characterized in that an inner surface of the branch flow passage connected to the aforementioned wells is subjected to a hydrophilic treatment.

[16] An invention is the sample analysis chip described in any one of [1] to [15] in which the sample analysis chip includes a first base material having the aforementioned well and the aforementioned flow passage formed therein and a second base material pasted together with the first base material.

[17] An invention is the sample analysis chip described in [16] characterized in that either one of the aforementioned base materials is formed of an optically transparent material.

[18] An invention is the sample analysis chip described in [17] characterized in that the first base material is an optically transparent resin material and the second base material is a metallic material.

[19] An invention is the sample analysis chip described in [17] characterized in that the first base material is formed of a resin that is optically transparent with respect to visible light and light absorptive with respect to infrared rays, and the second base material is a plate-shaped or film-shaped material that transmits infrared rays having a wavelength of at least 800 nm.

[20] An invention is the sample analysis chip described in [19] characterized in that the first base material is any one of the resin base materials among polypropylene resins, polycarbonate resins and acrylic resins.

[21] An invention is the sample analysis chip described in [19] or [20] characterized in that the first base material includes an infrared absorbing agent having an absorption peak within a wavelength region of at least 800 nm.

[22] An invention is the sample analysis chip described in any one of [1] to [3] characterized in that the second base material is any one of the resin base materials among polypropylene resins, polycarbonate resins and acrylic resins.

[23] An invention is the sample analysis chip described in any one of [1] to [22] characterized in that a thickness of the second base material is within a range from 0.05 to 0.5 mm.

[24] An invention is the sample analysis chip described in any one of [1] to [23] characterized in that a support portion for rotating a sample analysis chip is provided in the aforementioned first base material.

[25] An invention is a method of producing the sample analysis chip described in any one of [19] to [22] characterized by including irradiating an infrared laser from the aforementioned second base material side; and melting and bonding the aforementioned first base material and the aforementioned second base material, thereby pasting them together.

[26] An invention is the method of producing a sample analysis chip described in [25] characterized in that the aforementioned infrared laser has a wavelength within a range from 800 to 1,200 nm.

[27] An invention is the method of producing a sample analysis chip described in [25] or [26] characterized by including a step of fixing a reagent in the aforementioned wells before pasting together the aforementioned first base material and the aforementioned second base material during production of the sample analysis chip.

[28] An invention is a sample analyzer that includes a device for installing and rotating the sample analysis chip described in any one of [1] to [23] and a detecting and measuring device for detecting a reaction in the aforementioned well.

[29] An invention is a sample analysis method that includes a step for injecting a solution in the aforementioned main flow passage of the sample analysis chip described in any one of [1] to [23], and a step for rotating the sample analysis chip and thereby delivering the solution to each of the aforementioned wells.

[30] An invention is the sample analysis method described in [29] characterized by including a step for delivering a mineral oil to each of the aforementioned wells following the step for delivering the solution to each of the aforementioned wells.

[31] An invention is a genetic analysis method characterized by using the sample analysis method described in [29] or [30].

[Advantageous Effects of Invention]

Due to the sample analysis chip of the first embodiment according to the present invention, a simple and functional sample analysis chip which is also safe and cheap can be achieved. Moreover, one type of specimen can be subjected to a plurality of treatments.

Further, because the main flow passage is forming one peak between each well with respect to the rotation center, the liquid supply is interrupted at the peak portions in this main flow passage, thereby reducing variations in the liquid distribution. Moreover, by making the cross sectional area of these flow passage peak portions smaller, the variations at the time of liquid distribution can be reduced even further.

Furthermore, if the volume of the main flow passage from one flow passage peak portion to the other adjacent flow passage peak portion is designed arbitrarily, the equivalent volume of liquid sample can be supplied to the wells communicated with a flow passage valley portion sandwiched between the aforementioned flow passage peak portions, and thus the amount of sample solution used can be set arbitrarily for each well.

In addition, according to the sample analysis chip described in the second embodiment of the present invention, when the liquid is supplied from the main flow passages to the wells through centrifugal force, in the wells that received more than a predetermined amount of sample due to the variations in the liquid supply, a surplus can be discarded to the waste solution chamber. Accordingly, if more than a desired amount of liquid is supplied to all the wells, because the same amount of solution can be supplied to all the wells, variations in the liquid delivery can be reduced.

Furthermore, by providing a branch flow passage connected to the waste solution chamber to the side passage communicating with the main flow passage and the wells, contacts with the samples in other wells can be avoided, thereby suppressing contamination.

In addition, due to the sample analysis chip according to the third embodiment of the present invention, a small-sized, low-cost reaction chip can be achieved with a simple constitution. In the sample analysis chip of the present invention, by combining the first base material and the second base material and fusing them together through infrared laser, an enclosed-type chip hardly affecting the chip or the reagent fixed to the chip can be achieved.

BRIEF DESCRIPTION OF DRAWINGS

FIGS. 5A and 5B are plan views showing an arrangement of a side passage, a waste solution portion and a well in the sample analysis chip according to the second embodiment of the present invention.

FIG. 6 is a plan view of one aspect of the sample analysis chip according to the second embodiment of the present invention.

FIGS. 11A and 11B are plan views of a first base material that constitutes the sample analysis chip according to the third embodiment of the present invention.

FIG. 12 is a cross sectional view of a flow passage and a well in an embodiment for the sample analysis chip according to the third embodiment of the present invention.

DESCRIPTION OF EMBODIMENTS

A sample analysis chip according to the first embodiment of the present invention will be descried with reference to the drawings.

Figure 1:
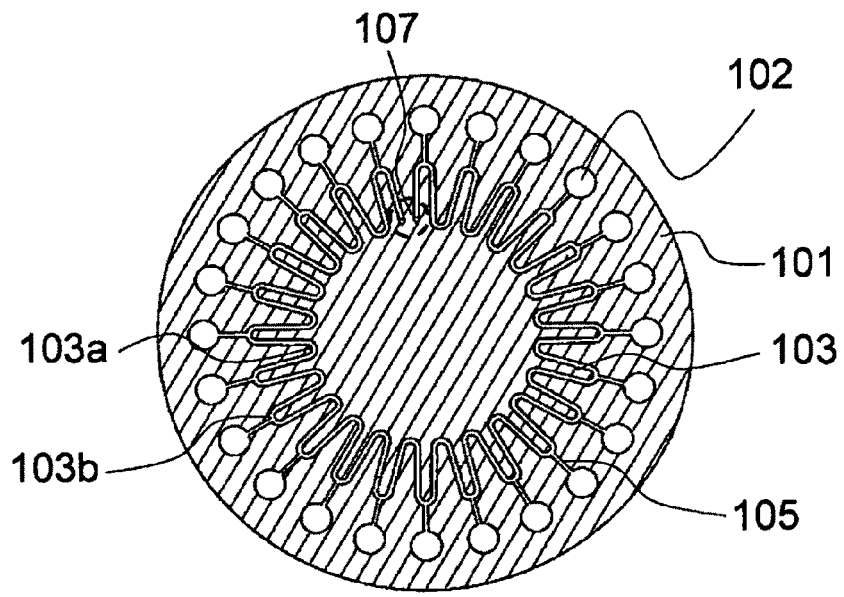
FIG. 1 is a plan view of one aspect of a sample analysis chip according to a first embodiment of the present invention.

FIG. 1 is a plan view showing one aspect of a sample analysis chip according to the present invention. The chip of the present invention has, on top of a base material 101, a plurality of wells 102 and flow passages for supplying a solution, for example, a liquid sample (solution), to the wells. In order to supply liquids to each well, the flow passages include at least one main flow passage 103 communicating with each well, as well as a side passage 105 that connects the main flow passage and the wells. The flow passages have an inlet for injecting a solution. In the aspect depicted in FIG. 1, the main flow passages have an injection port (INLET) at one end and an exit (OUTLET) for a surplus solution at the other end which also serves as an air exit.

The sample analysis chip of the present invention delivers liquid to the respective wells 102 through the centrifugal force caused by rotating the chip, and thus preferably has a disc shape having a point penetrated by the axis of rotation at the center (hereafter, referred to as a central point). However, there are no particular limitations as long as it is formed so as to be rotatable with respect to the axis of rotation that penetrates the chip. If it has a disc shape, the space can be used efficiently because it is possible to arrange the wells concentrically on this disc-shaped chip by making the center to serve as the axis of rotation. It is important to apply the centrifugal force uniformly in order to deliver liquids to the wells uniformly. This can easily be achieved by designing the chip so as to have rotational symmetry, except the INLET/OUTLET regions 107, with the central point serving as the axis. In other words, if there are N wells, the centrifugal force can be applied uniformly when the symmetry is N-fold. Needless to say, this is not the case when the amount of liquid delivered to each well is different. In addition, because the wells are arranged concentrically, analysis for all wells can be conducted at one single examination area by rotating the base material.

The main flow passage 103 is formed closer to the central point side than the wells. Moreover, the sample analysis chip of the present invention is characterized in that this main flow passage is formed so as to have one peak between the neighboring wells in the direction of the central point. Here, the neighboring wells refer to the wells that are present upstream and downstream of the main flow passage, through the flow passages that supply liquids to the wells. Further, the expression "have a peak in the direction of the central point" means that a local maximum point (main flow passage peak portion 103a) is present in the direction of the central point. By forming the main flow passage so as to have one peak between the neighboring wells in the direction of the central point as described above, the flow of liquid injected into the main flow passage is interrupted naturally at the main flow passage peak portion during chip rotation, thereby reducing variations in the amount of liquid delivered to each well.

The communicating place for the wells 102 and the main flow passage 103, that is, the connecting place for the main flow passage 103 and the side passage 105 preferably corresponds to a valley portion 130b between the peak portions of the main flow passage. The valley portion refers to a place between the peaks of the main flow passage which is farthest from the central point. By configuring the wells and the main flow passage to communicate at this place, the amount of residual solution in the main flow passage during the liquid delivery can be reduced.

Further, the communicating port of the main flow passage 103 and the wells 102 needs to have a width and cross sectional area of certain extent so as to prevent the solution from entering the wells at a stage prior to the chip rotation, as described later in the processing method using the sample analysis chip.

Furthermore, it is preferable that the wells 102 connect with the main flow passage at a point which is closest to the central point of the wells in order to prevent air from remaining inside the wells. In other words, when forming a side passage 105, it is preferable to form so as to link the point in the well side which is closest to the central point and the valley portion in the flow passage side.

Figure 2:
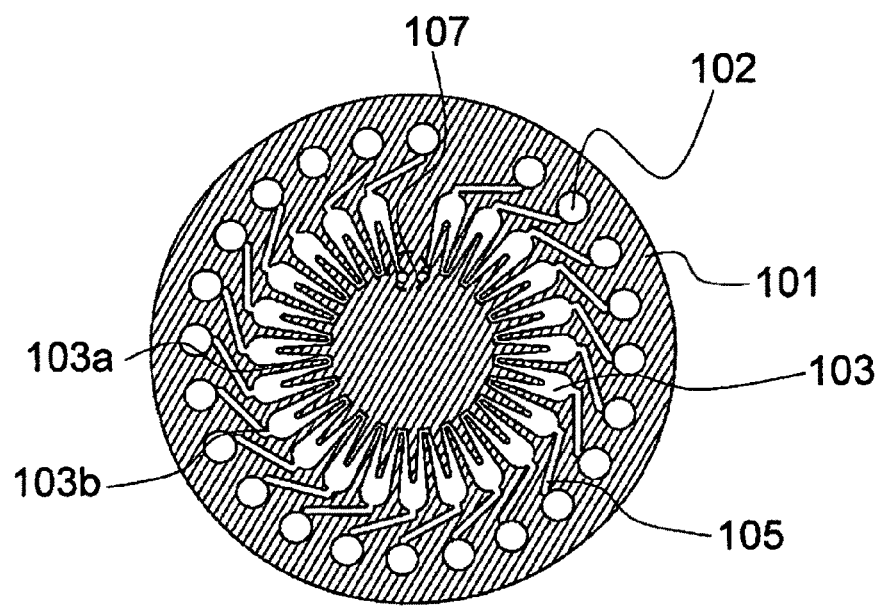
FIG. 2 is a plan view of one aspect of a sample analysis chip according to the first embodiment of the present invention.

FIG. 2 is a plan view showing another aspect of the sample analysis chip according to the present invention. In the aspect depicted in FIG. 2, the passage width of the main flow passage is narrow in the main flow passage peak portion 103a and wide in the main flow passage valley portion 103b. The less the solution present in the region corresponding to the main flow passage peak portion 103a, the less the variations in liquid delivery. Accordingly, the cross sectional area of the main flow passage in the peak portion is preferably smaller than the cross sectional area thereof in other parts. Therefore, it is preferable to make the width of the flow passage narrow and/or to make the depth shallow, in the peak portion. Further, it is preferable that the cross sectional area of the main flow passage reduce as it approaches the peak portion due to the same reason.

Furthermore, the amount of liquid delivered to each well 102 can be controlled by widening the passage width of the main flow passage valley portion 103b. Accordingly, by making the flow passages between the peaks into a chamber-like form as in the sample analysis chip depicted in FIG. 3 and arbitrarily designing the volume of the main flow passage from one main flow passage peak portion to the adjacent main flow passage peak portion, an equal volume of liquid sample can be supplied to the wells from the communicating valley portion that is sandwiched between the two peak portions, and thus the amount of sample solution can be set arbitrarily for each well.

Further, the volume of the wells 102 is preferably not less than 1 μl and not more than 100 μl. When the volume is less than 1 μl, the centrifugal force does not apply sufficiently, making the liquid supply to wells difficult, whereas the volume exceeding 100 μl may reduce the mixing properties of reagents or reduce uniformity of the temperature inside the wells.

Further, in the aspect depicted in FIG. 2, the side passage 105 is formed so as to be inclined with respect to the direction of the central point. By forming the side passage in an inclined manner as described above, when the centrifugal force is applied, air inside the well moves along the inner side of the side passage towards the main flow passage direction while the solution moves along the outer side of the side passage towards the well direction. Accordingly, the solution can be moved smoothly into the well. In terms of the inclination angle, it is preferable that an angle formed between the direction of the central point and the side passage be from 10 degrees to 80 degrees. When the angle is less than 10 degrees, the evacuation of air from the well interferes with the entry of solution thereto, which may prevent the entry of solution. On the other hand, when the angle exceeds 80 degrees, the centrifugal force applied to the side passage direction is weak so that the solution does not move to the well at times.

Figure 3:
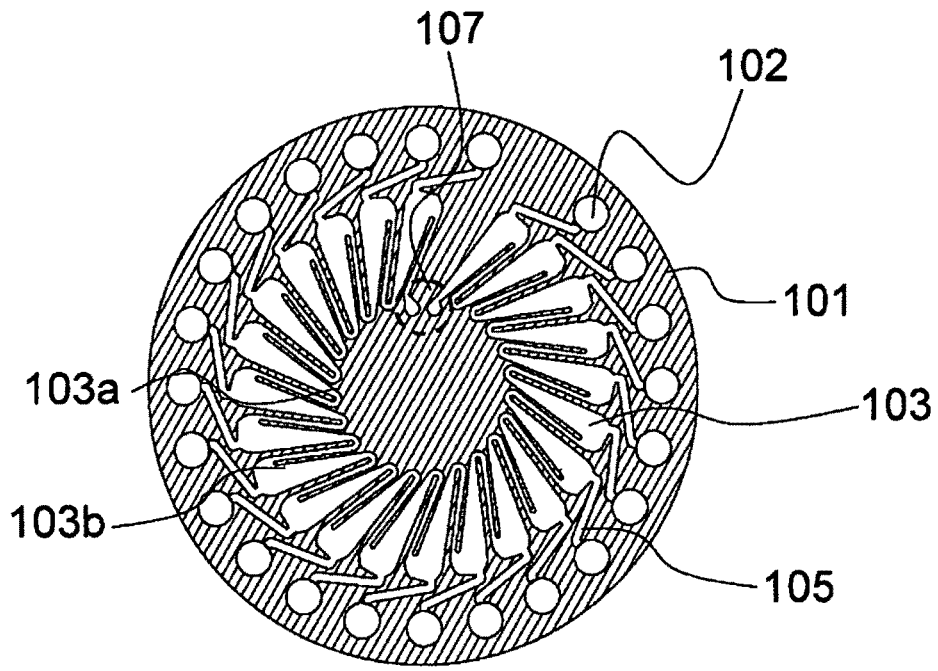
FIG. 3 is a plan view of one aspect of a sample analysis chip according to the first embodiment of the present invention.

FIG. 3 is a plan view showing yet another aspect of the sample analysis chip according to the present invention. In the sample analysis chip illustrated in FIG. 3, the peak of the main flow passage 103 is inclined with respect to the central point direction. Accordingly, it is designed so that the areas within the base material plane on the left and right sides of the main flow passage with respect to the side passage 105 are unequal. The main flow passage consists of a flow passage side with a narrow passage width and a flow passage side with a wide passage width on the left and right sides with respect to the side passage 105, and the side passage 105 serving as a communication port with the well is formed on the wide flow passage side. As a result, at the time of exchange between the air moved from the well to the side passage and the solution in the main flow passage, the exchange of air bubbles and solution occurs disproportionately in the main flow passage side with a large area. For this reason, the amount of residual solution in the main flow passage can be reduced. Accordingly, by configuring the side passage connected to each well and the main flow passage as described above and forming the main flow passage so that the flow passage side with a narrow passage width and the flow passage side with a wide passage width are arranged alternately with the peak portion sandwiched therebetween as a boundary, the same phenomenon occurs simultaneously in each chamber-like main flow passage, thereby reducing variations in the liquid delivery.

A sample analysis chip according to the second embodiment of the present invention will be descried with reference to the drawings.

Figure 4:
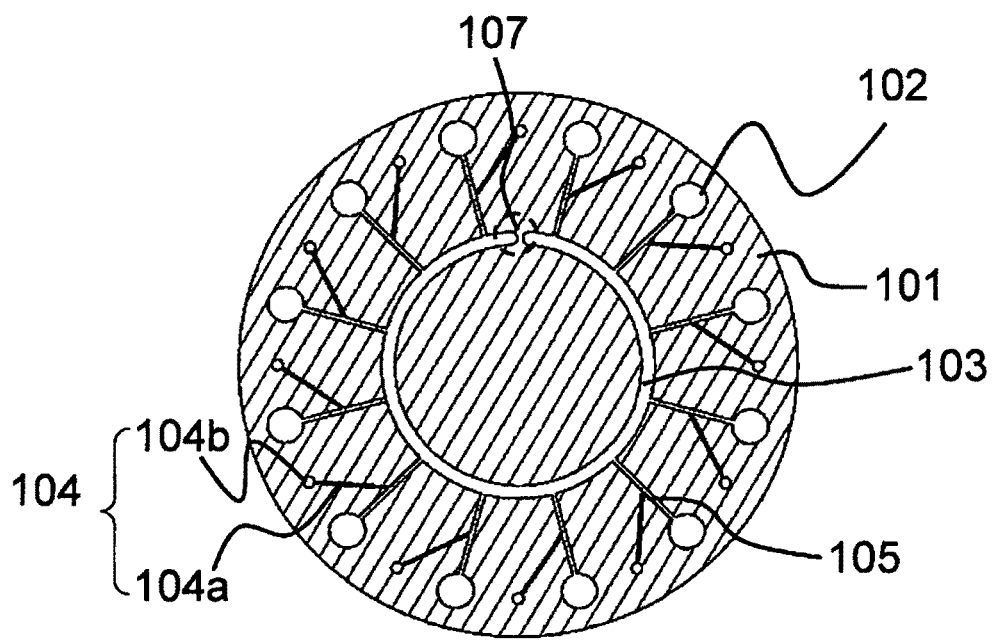
FIG. 4 is a plan view of one aspect of a sample analysis chip according to a second embodiment of the present invention.

FIG. 4 is a plan view showing one aspect of a sample analysis chip according to the present invention. The chip of the present invention has, on top of a base material 101, a plurality of wells 102 and flow passages for supplying a solution such as a liquid sample (solution) to the wells. In order to supply liquids to each well, the flow passages include at least one main flow passage 103 communicating with each well, as well as a side passage 105 that connects the main flow passage and the wells. The flow passages have an inlet for injecting a solution. In the aspect depicted in FIG. 4, the main flow passages have an injection port (INLET) at one end and an exit (OUTLET) for a surplus solution at the other end which also serves as an air exit.

The sample analysis chip of the present invention delivers liquids to the respective wells 102 through the centrifugal force caused by rotating the chip, and thus preferably has a disc shape having a point penetrated by the axis of rotation at the center (hereafter, referred to as a central point). However, there are no particular limitations as long as it is formed so as to be rotatable with respect to the axis of rotation that penetrates the chip. If it has a disc shape, the space can be used efficiently because it is possible to arrange the wells concentrically on this disc-shaped chip by making the center to serve as the axis of rotation. It is important to apply the centrifugal force uniformly in order to deliver liquids to the wells uniformly. This can easily be achieved by designing the chip so as to have rotational symmetry, except the INLET/OUTLET regions 107, with the central point serving as the axis. In other words, if there are N wells, the centrifugal force can be applied uniformly when the symmetry is N-fold. Needless to say, this is not the case when the amount of liquid delivered to each well is different. In addition, because the wells are arranged concentrically, analysis for all wells can be conducted at one single examination area by rotating the base material.

The main flow passage 103 is formed closer to the central point side than the wells 102. The communicating port of the main flow passage 103 and the wells 102 needs to have a width and cross sectional area of certain extent so as to prevent the solution from entering the wells at a stage prior to the chip rotation, as described later in the processing method using the sample analysis chip. Although depending on the type of solution to be used since the surface tension is involved, when the solvent is water, for example, an area of not more than 2×2 mm$^2$ satisfies this condition.

The volume of the wells 102 is preferably not less than 1 μl and not more than 100 μl. When the volume is less than 1 μl, the centrifugal force does not apply sufficiently, making the liquid supply to wells difficult, whereas the volume exceeding 100 μl may reduce the mixing properties of reagents or reduce uniformity of the temperature inside the wells.

Furthermore, it is preferable that the wells 102 connect with the main flow passage at a point which is closest to the central point of the wells in order to prevent air from remaining inside the wells. In other words, it is preferable to form so that the side passage 105 connect with the well side at a point which is closest to the central point.

Furthermore, in the sample analysis chip of the present invention, in the side passage 105 that connects each well 102 and the main flow passage 103, a waste solution portion 104 is provided for each side passage. The waste solution portion can be constituted of a waste solution branch flow passage 104a branched from the side passage and a waste solution chamber 104b connected to the branched waste solution flow passage. Because the waste solution portion is provided in the side passage that communicates the well 102 and the main flow passage 103, when an excessive amount of solution is supplied to the well, the surplus solution is transferred to and stored in the waste solution portion, thereby leaving a certain volume of solution in the well and in a well branch flow passage 105a. Accordingly, variations in the liquid delivery due to the surplus solution can be reduced.

By filling the well 102 with a solution prior to the waste solution chamber 104b during the liquid delivery, a solution sample can reliably be loaded to each well. For this reason, it is important to configure so that the liquid is more easily supplied to the well branch flow passage than to the waste solution chamber branch flow passage.

A method for achieving this involves making the cross sectional area of the well branch flow passage 105a larger than that of the waste solution chamber branch flow passage 104a, thereby creating the difference in pressure loss during liquid supply and preferentially supplying liquids to the well. Due to this technique, the well is first filled with a solution, and then the surplus solution can be supplied to the waste solution chamber. Accordingly, by configuring the waste solution portion from the waste solution chamber branch flow passage 104a having a small cross sectional area and the waste solution chamber 104b having a large capacity, liquids can be easily supplied to the well branch flow passage side, and also the capacity of the waste solution portion can be adjusted. Note that the amount of waste solution from the surplus solution can be controlled through the capacity of the well and the capacity of the waste solution chamber. The required capacity of the waste solution chamber increases as the variations among the respective wells increase during the centrifugal liquid supply.

Another method involves making the surface roughness inside the well branch flow passage lower than that of the waste solution chamber branch flow passage, thereby creating the difference in pressure loss during liquid supply and preferentially supplying liquids to the well.

Further, yet another method involves subjecting the surface of the waste solution chamber branch flow passage to a water repellency treatment, thereby creating the difference in pressure loss during liquid supply and preferentially supplying liquids to the well. Alternatively, by subjecting the surface of the well branch flow passage to a hydrophilic treatment, the difference in pressure loss can be created during liquid supply, thereby preferentially supplying liquids to the well. Methods for the water repellency treatment typically involve a coating process using a fluorine-based material or the like, which exhibit a high level of chemical resistance and cause no adverse effects on the reaction. Further, examples of techniques for the hydrophilic treatment include a plasma treatment and a corona discharge treatment, both of which are general techniques.

Furthermore, liquids can also be supplied preferentially to the well branch flow passage side due to the shape of the side passage 105 and the arrangement of waste solution portion 104. FIGS. 5(A) and 5(B) are diagrams schematically showing a waste solution portion constituted of the side passage 105, the well 102, the waste solution chamber 104b and the waste solution chamber branch flow passage 104a. The solid arrow indicates the direction of the central point (direction of the rotation center).

The side passage 105 is formed so as to be inclined with respect to the direction of the rotation center in the respective configurations depicted in FIG. 5. By forming the side passage in an inclined manner as described above, when the centrifugal force is applied, air inside the well 102 moves along the inner side of the side passage towards the main flow passage direction while the solution moves along the outer side of the side passage towards the well direction. Accordingly, the solution can be moved smoothly into the well. In terms of the inclination angle, it is preferable that an angle formed between the direction of the central point and the side passage be from 10 degrees to 80 degrees. When the angle is less than 10 degrees, the evacuation of air from the well interferes with the entry of solution thereto, which may prevent the entry of solution. On the other hand, when the angle exceeds 80 degrees, the centrifugal force applied to the side passage direction is weak so that the solution does not move to the well at times.

With respect to the inclined side passage 105 illustrated in FIGS. 5(A) and 5(B), the waste solution portion 104 is branched from the side passage 105 on the central point side through the waste solution chamber branch flow passage 104a. FIG. 5(A) shows a pattern in which the side passage 105 is extended straight towards the well 102, whereas FIG. 5(B) shows a pattern in which the side passage on the well side (i.e., the well branch flow passage 105a) is bent at the branching point from the waste solution portion. The bent waste solution chamber branch flow passage 104a can be formed into any shape as long as it is inclined in the same direction as the slope of the side passage before bifurcation. Further, when the capacity of the waste solution chamber branch flow passage portion is sufficient for accommodating the waste solution, the waste solution chamber 104b at the end of the waste solution portion may be omitted.

As described earlier, the centrifugal force is applied to the solution causing a flow from the central point and first into the flow passage on the outer side, that is, the branch flow passage towards the well side, as indicated by the dashed arrow. As a result, the well 102 is filled with a solution prior to the waste solution chamber 104b so that a solution sample can reliably be loaded to each well. Further, when the flow passage on the well side is bent as illustrated in FIG. 5(B), because the well branch flow passage 105a can be made small, or the well can be connected directly at the branching point of the side passage, the flow passage for supplying the surplus solution to the waste solution chamber after loading the well with the solution can be shortened, thereby further reducing the variations of liquid delivery to the well.

Figure 7:
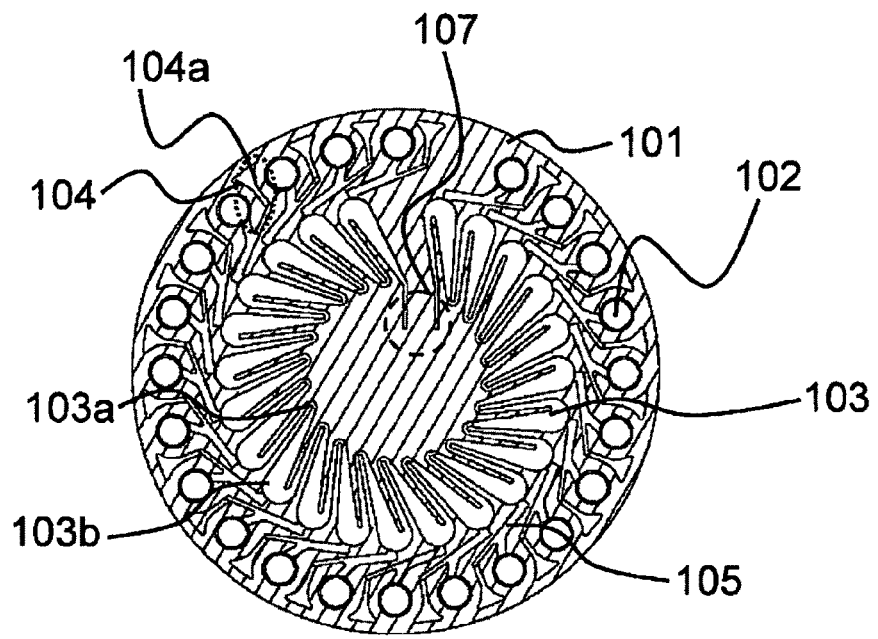
FIG. 7 is a plan view of one aspect of the sample analysis chip according to the second embodiment of the present invention.

On the other hand, when the amount of solution is smaller than the predetermined volume, variations of sample volume among the respective wells cannot be reduced by the waste solution portion. However, by modifying the shape of the main flow passage, variations in the amount of supplied liquid at the time of original liquid supply can be suppressed. For example, a sample analysis chip of an aspect combined with the sample analysis chip of the first embodiment according to the present invention can be prepared. Other modes of such sample analysis chips of the present invention are shown in FIG. 6 and FIG. 7.

It should be noted that the items and components of the sample analysis chip according to the first embodiment which are not described in the following aspect can be combined, as long as they do not contradict with the second embodiment, to prepare the sample analysis chip of the present invention.

In the sample analysis chip illustrated in FIG. 6, the main flow passage 103 is formed so as to have one peak between the neighboring wells in the direction of the central point. Here, the neighboring wells refer to the wells that are present upstream and downstream of the main flow passage, through the flow passages that supply liquids to the wells. Further, the expression "have a peak in the direction of the central point" means that a local maximum point (main flow passage peak portion 103a) is present in the direction of the central point. By forming the main flow passage so as to have one peak between the neighboring wells in the direction of the central point as described above, the flow of liquid injected into the main flow passage is interrupted naturally at the main flow passage peak portion during chip rotation, thereby reducing variations in the amount of liquid delivered to each well.

The communicating place for the wells 102 and the main flow passage 103, that is, the connecting place for the main flow passage 103 and the side passage 105 preferably corresponds to a valley portion 130b between the peak portions of the main flow passage. The valley portion refers to a place between the peaks of the main flow passage which is farthest from the central point. By configuring the wells and the main flow passage to communicate at this place, the amount of residual solution in the main flow passage during the liquid delivery can be reduced.

Further, in the sample analysis chip illustrated in FIG. 6, the main flow passage 103 is formed so as to the passage width of the main flow passage 103 is narrow in the main flow passage peak portion 103a and wide in the main flow passage valley portion 103b. The less the solution present in the region corresponding to the main flow passage peak portion 103a, the less the variations in liquid delivery. Accordingly, the cross sectional area of the main flow passage in the peak portion is preferably smaller than the cross sectional area thereof in other parts. Therefore, it is preferable to make the width of the flow passage narrow and/or to make the depth shallow, in the peak portion. Further, it is preferable that the cross sectional area of the main flow passage reduce as it approaches the peak portion due to the same reason.

Furthermore, the amount of liquid delivered to each well 102 can be controlled by widening the passage width of the main flow passage valley portion 103b. Accordingly, by making the flow passages between the peaks into a chamber-like form as in the sample analysis chip depicted in FIG. 2 and arbitrarily designing the volume of the main flow passage from one main flow passage peak portion to the adjacent main flow passage peak portion, an equal volume of liquid sample can be supplied to the wells from the communicating valley portion that is sandwiched between the two peak portions, and thus the amount of sample solution can be set arbitrarily for each well.

FIG. 7 shows another aspect of the sample analysis chip according to the present invention. In the sample analysis chip illustrated in FIG. 7, the peak of the main flow passage 103 is inclined with respect to the central point direction. Accordingly, it is designed so that the areas within the base material plane on the left and right sides of the main flow passage with respect to the side passage 105 are unequal. The main flow passage consists of a flow passage side with a narrow passage width and a flow passage side with a wide passage width on the left and right sides with respect to the side passage 105, and the side passage 105 serving as a communication port with the well is formed on the wide flow passage side. As a result, at the time of exchange between the air moved from the well to the side passage and the solution in the main flow passage, the exchange of air bubbles and solution occurs disproportionately in the main flow passage side with a large area. For this reason, the amount of residual solution in the main flow passage can be reduced. Accordingly, by configuring the side passage connected to each well and the main flow passage as described above and forming the main flow passage so that the flow passage side with a narrow passage width and the flow passage side with a wide passage width are arranged alternately with the peak portion sandwiched therebetween as a boundary, the same phenomenon occurs simultaneously in each chamber-like main flow passage, thereby reducing variations in the liquid delivery.

Next, a method of producing the sample analysis chip of the present invention according to the first and second embodiments will be described.

Figure 8:
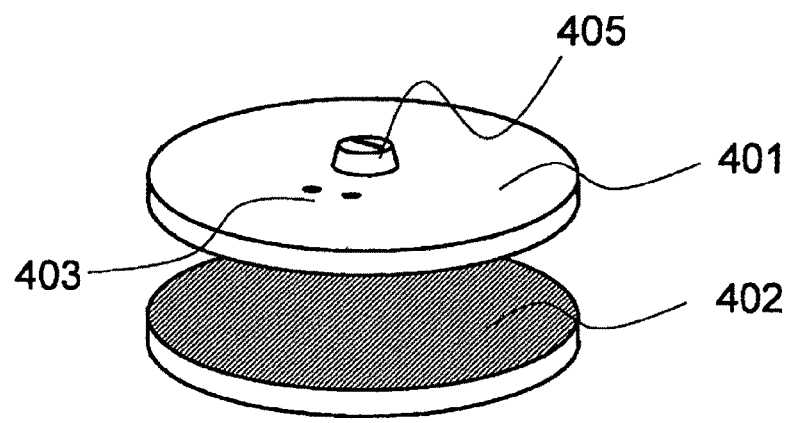
FIG. 8 is a perspective view for the explanation of a sample analysis chip of the present invention.

FIG. 8 is a perspective view showing an aspect of the structure for the sample analysis chip according to the present invention.

The sample analysis chip of the present invention can be prepared by pasting a second base material 402 with a first base material 401 having wells and flow passages (including a main flow passage and a side passage) formed therein. At least one of the first base material and the second base material has, as a rotating means for rotating a chip through a chip rotating mechanism provided in a sample analysis apparatus, for example, a support portion 405 for fixing the chip onto the chip rotating mechanism. In addition, at least one through hole for an injection port and an exit which also serves as an air exit (INLET/OUTLET) is formed in one of the first base material and the second base material. The through hole coincides with the end portion of the main flow passage when the base materials are pasted together. In the description below, for the sake of simplicity, when detecting or measuring a fluorescence reaction or the like, the side of the base material positioned in the measured plane is referred to as an "upper side" and the side of the other base material positioned below is referred to as a "lower side".

Although there are no particular limitations on the base material so long as it does not adversely affect the sample, when a resin material containing any one of polypropylene, polycarbonate and acryl is used, satisfactory transmission properties for visible light can be ensured. As the polypropylene, a homopolypropylene or a random copolymer of polypropylene and polyethylene can be used. Further, as the acryl, polymethylmethacrylate or a copolymer consisted of methyl methacrylate and another monomer, such as methacrylate esters, acrylate esters and sryrene, can be used. In addition, when these resin materials are used, the heat resistance and strength for the chip can also be ensured. Apart from the resin materials, metallic materials such as aluminum, copper, silver, nickel, brass and gold can be used. In those cases where the metallic materials are used, the thermal conductivity and the sealing performance can be further improved. Note that by making the bottom of the well transparent at least in the base material on the upper side, among the base materials that are pasted together, detection and analysis of fluorescence and the like can be conducted from the outside. It should be noted that the terms "transparent" and "optically transparent" used in the present invention refers to an average transmittance of the detected light within the wavelength region of not less than 70%. It is easy to visually observe the conditions of the sample inside the chip if a material that is optically transparent within the visible light region (from 350 to 780 nm in wavelength) is used, although the present invention is not limited to these cases.

In terms of the method of processing the base material for forming the wells, the flow passages and the waste solution portion, when a resin material is used, various resin molding processes such as injection molding and vacuum molding or mechanical cutting can be employed. When a metallic material is used, the wells, the flow passages and the waste solution portion can be formed by subjecting a thick base material to a grinding or etching process, or subjecting a thin metallic sheet to a pressing or squeezing process.

Further, when a resin material containing any one of polypropylene, polycarbonate and acryl is used as the first base material, satisfactory optical transparency, heat resistance and strength can be ensured. In addition, when the first base material has a thickness within the range of 50 μm to 3 mm, satisfactory optical transparency, heat resistance and strength can be ensured and processing of the recess portion can be reliably conducted.

Moreover, when the second base material has a thickness within the range of 10 μm to 300 μm, it is possible to satisfy both heat conductivity and sealing properties of the second base material. When the thickness of the second base material is more than 300 μm, heat capacity increases, which may deteriorate the heat responsiveness.

Figure 9:
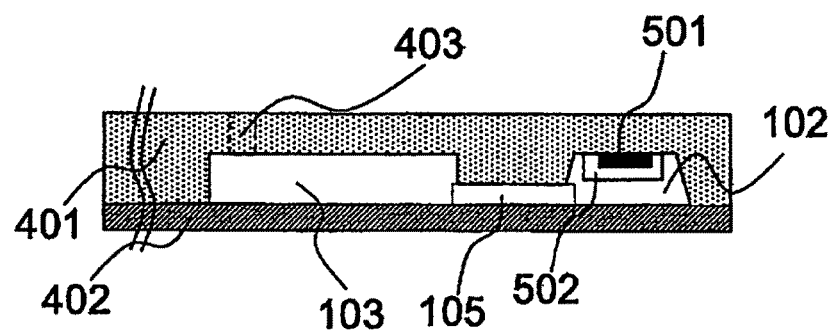
FIG. 9 is a cross sectional view for the explanation of a sample analysis chip of the present invention.

FIG. 9 shows a cross sectional view of the sample analysis chip according to the present invention. In the first base material 401, an injection port 403 for the solution which penetrates the chip, a groove 103 which is to become a main flow passage for letting the injected solution to flow into the chip, a groove 105 which is to become a side passage communicating with each well extended to the outer periphery of the chip, and a pit 102 which is to become a well in the outer periphery of the chip are formed. Note that the cross sectional view of FIG. 9 is a drawing schematically showing a pathway from the injection port (INLET/OUTLET) to the well, and the shapes of the main flow passage and the side passage are not limited to those shown in this drawing. In order to fill all the wells with the injected solution, the volume of the main flow passage needs to be larger than the sum of the volume of the respective wells. However, when a reagent 501 is fixed in the well, the amount of liquid sample charged into the reaction well reduces due to this, and thus the volume of flow passage through which the liquid flows may be reduced by the same extent. In those cases where the detection and measurement of fluorescence reactions are conducted on the first base material side, it is preferable that the recess portion of the well have a smooth shape so as not to scatter light.

The reagent 501 for reaction is fixed in the well 102 before pasting together the base materials. Different types of reagents can be used in each well. By fixing different types of reagents in the respective reaction wells, one type of specimen (sample) can be subjected to a plurality of treatments. Further, it may also be configured so that a portion of the reagent for actually carrying out the reaction is fixed in each well while the remaining reagent is introduced together with the liquid sample.

In terms of the fixing method for the reagent 501, for example, a liquid reagent is added dropwise to the well portion of the first base material using a pipette or the like, and the first base material 401 is then centrifuged using a centrifugal apparatus at 2,000 to 3,000 rpm for about 5 minutes. As a result, an adequate amount of liquid reagent remains in a state where the liquid level is flat, and by drying this, the reagent can be fixed in the well.

Further, a wax 502 may be added dropwise following fixation of the reagent in the well. More specifically, the wax is melted on a hot plate and added dropwise using a pipette so as to cover the dried reagent. At this time, the wax is solidified within a few seconds. The wax has a role in fixing the reagent in the recess portion of the well.

Examples of the methods for pasting the base materials together include a method in which a resin coating layer that serves as an adhesive layer is provided in one base material, and both the base materials are bonded by melting this layer. It is preferable to provide the resin coating layer in a metallic base material having high thermal conductivity for the melting and bonding. As a material for the resin coating layer, resin materials such as PET, polyacetal, polyester and polypropylene can be used.

In this pasting method, it is preferable to use a resin material which is readily microfabricated and exhibits an optical transparency suitable for the fluorescence measurement as the first base material, and to use a metallic material provided with a resin coating layer as the second base material, which exhibits high thermal conductivity and can be pasted easily through melting and bonding. Moreover, by forming the resin coating layer on the surface of the metallic base material, the chemical resistance of the metallic base material itself may not be taken into account when selecting materials.

In addition, during formation of a resin coating layer on the surface of the base material, by forming an anchor layer as a base for the resin coating layer, fusion using a laser can be conducted. The anchor layer contains carbon black (light absorbing material) kneaded therein which absorbs light having a laser wavelength and generates heat when being irradiated by a laser beam so as to melt the resin coating layer for bonding. Alternatively, instead of adding carbon black to the anchor layer, carbon black may be added to the resin coating layer, or the surface of the resin coating layer may be painted black. The resin coating layer can also be efficiently melted by, for example, irradiating an infrared photodiode laser beam having a wavelength of about 900 nm. Unlike the thermal welding, the base materials can be pasted together through the laser welding without affecting the chip or the reagents fixed to the chip since there is no need to heat the chip.

A sample analysis chip according to the third embodiment of the present invention as well as the production method therefor will be descried with reference to the drawings.

It should be noted that for the sake of simplicity, when detecting or measuring a fluorescence reaction or the like, the side of the base material positioned in the measured plane is referred to as an "upper side" and the side of the other base material positioned below is referred to as a "lower side".

Figure 10:
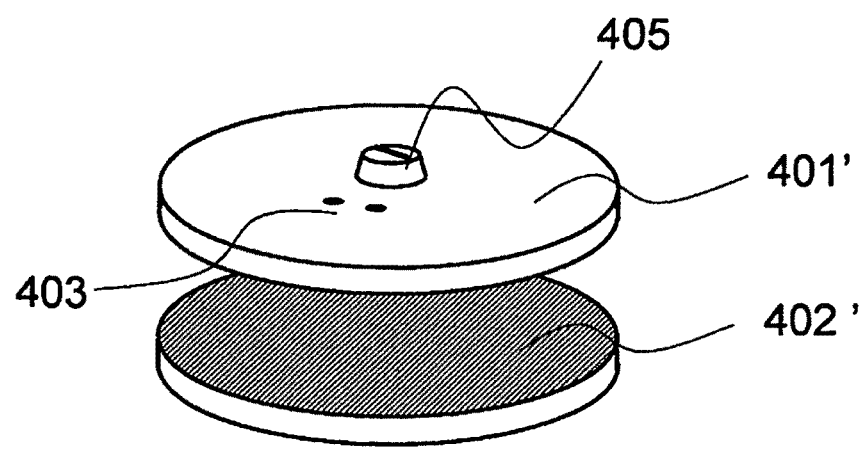
FIG. 10 is a perspective view of a sample analysis chip according to a third embodiment of the present invention.

FIG. 10 is a perspective view of a sample analysis chip according to the third embodiment of the present invention. In the sample analysis chip of the present invention according to the embodiment illustrated in FIG. 10, a first base material 401' in the upper side and a second base material 402' in the lower side are formed so that these two members are combined. In the first base material, a flow passage for supplying solutions such as reagents and a well for reacting the solutions and the reagents are formed. In addition, in the first base material or the second base material, at least one through hole 403 is provided as an injection port for injecting a solution into the formed flow passage and an exit which also serves as an air exit.

An example of the well 102 and the flow passages (the main flow passage or injection section 103 and the side passage 105) formed on top of the first base material is shown in FIG. 11. The chip of the present invention has, on top of the base material 101, a plurality of wells 102 in the outer periphery and flow passages for supplying a solution such as a liquid sample to the wells. The flow passages include the main flow passage or injection section 103 in the form as illustrated in FIG. 11A or FIG. 11B for injecting a solution from the injection port, and the side passage 105 that communicates the main flow passage or injection section with the wells in order to deliver liquids to the respective wells.

In addition, the sample analysis chip according to the third embodiment of the present invention can be prepared by combining the items and components of the present invention according to the first and second embodiments as long as they do not contradict with each other. For example, the shape of the main flow passage 103 can be made into a wave-like form as shown in the first embodiment, or the side passage 105 may be configured so as to have a waste solution portion. Further, constitutions other than those of the first or second embodiment may also be combined.

The sample analysis chip of the present invention delivers liquids to the respective wells 102 through the centrifugal force caused by rotating the chip. The advantages associated with the supply of liquids through the centrifugal force are that installation of an opening for evacuation in the respective wells 102 is not required, and the liquid sample can enter the respective wells, due to the centrifugal force, by replacing the air present in the wells. As a result, the sealing properties of the wells can be improved, thereby preventing the contamination from the outside. Because the chip is rotated, the shape of the chip is preferably a disc shape having a point penetrated by the axis of rotation at the center (hereafter, referred to as a central point). However, there are no particular limitations as long as it is formed so as to be rotatable with respect to the axis of rotation that penetrates the chip. If it has a disc shape, the space can be used efficiently because it is possible to arrange the wells concentrically on this disc-shaped chip by making the center to serve as the axis of rotation. In addition, because the wells are arranged concentrically, analysis for all wells can be conducted at one single examination area by rotating the base material.

As a rotating means for rotating a chip through an external rotating mechanism, for example, the support portion 405 as illustrated in FIG. 10 is provided in the first base material.

The sample analysis chip of the present invention is constituted of a first resin base material 401' which is an optically transparent resin base material transmitting visible light, and a second resin base material 402' exhibiting infrared transparency. By configuring in such a manner so that the interfacial portion between the first base material and the second base material is melted for bonding by the infrared laser, the sample analysis chip can be produced. Compared to the thermal welding, the greatest advantage of the laser welding is that the chips or the reagents fixed to the chips are hardly affected at the time of chip production. Compared to the cases where a pressure sensitive adhesive is used, reagents inside the wells are free from the contamination caused by the adhesive, and the heat resistance and water resistance of the welded chip can be sufficiently ensured. A more detailed description is provided below.

In order to carry out the fluorescence measurements of wells, it is necessary that at least the wells 102 of the first base material 401' positioned in the measured plane side exhibit an optical transparency to transmit the visible light having a wavelength of no more than 750 nm. The optical transparency is preferably such that the average transmittance is at least 50%, and more preferably no less than 70%, within the fluorescence wavelength region. For this reason, it is preferable to use a resin material containing any one of polypropylene, polycarbonate and acryl as the first base material. A satisfactory level of optical transparency for the visible light can be ensured by using these materials. As the polypropylene, a homopolypropylene or a random copolymer of polypropylene and polyethylene can be used. Further, as the acryl, polymethylmethacrylate or a copolymer consisted of methyl methacrylate and another monomer, such as methacrylate esters, acrylate esters and sryrene, can be used. In addition, when these resin materials are used, the heat resistance and strength for the chip can also be ensured.

Further, when the first base material 401' has a thickness within the range of 0.05 mm to 3 mm, satisfactory levels of optical transparency for visible light, heat resistance and strength can be ensured and processing of the flow passages and the wells can be reliably conducted. Note that various resin molding processes such as injection molding and vacuum molding or mechanical cutting can be employed for the first base material. By forming the wells 102, the flow passages and the support portion 405 in the first base material side, the second base material to be irradiated with infrared rays can be prepared as a plate-like or film-like base material, which can be pasted together without fusion irregularities as described later. Further, at least the bottom of the well in the first base material is formed into a flat plane for the optical measurements of fluorescence reactions or the like.

In addition, when fusing the first base material 401' and the second base material 402' by the infrared laser, in order to improve the laser welding efficiency, it is preferable that the first base material exhibit light absorbing properties with respect to the infrared laser. At least a portion of the first base material containing the pasted plane absorbs infrared rays so that the resin can be easily melted and bonded.

Further, by including an infrared absorbing agent in the first base material 401', the infrared laser beam is absorbed, and the efficiency to convert light energy of infrared rays to thermal energy can be enhanced. Moreover, by including an infrared absorbing agent, a resin exhibiting no infrared absorption can be used. The infrared laser beam can be typically obtained by employing a semiconductor laser having a wavelength of at least 750 nm. Accordingly, as the infrared absorbing agent, a compound having an absorption maximum within the wavelength region of not less than 750 nm, i.e., a so-called pigment compound can be used. The pigment compounds can be generally classified into two types; i.e., dyes and pigments, and dye-type compounds are preferred in view of the compatibility with the resin base material and the transparency. Moreover, in order to ensure the transparency in the visible light region, it is preferable that light absorption by the infrared absorbing agent in the visible light region of not more than 750 nm be as less as possible. Specific examples include Lumogen (registered trademark) IR765 and Lumogen (registered trademark) IR788 manufactured by BASF.

For example, when polypropylene is used as the resin base material, since polypropylene does not exhibit absorption in the infrared region, it is necessary to add an infrared absorbing agent to a propylene resin. More specifically, as an example, 0.01 parts by weight of an infrared absorbing agent is added and compounded in advance, relative to 100 parts by weight of a propylene resin, thereby preparing a propylene resin pellet containing an infrared absorbing agent. By using this pellet, the first base material for the sample analysis chip of the present embodiment can be prepared through injection molding. Moreover, 0.1 parts by weight of an infrared absorbing agent is added in advance, relative to 100 parts by weight of a propylene resin, thereby preparing a propylene resin master batch containing an infrared absorbing agent. In addition, when performing injection molding, the aforementioned propylene resin master batch containing an infrared absorbing agent and a propylene resin are mixed at a certain ratio to carry out injection molding so that the content of infrared absorbing agent can be adjusted.

The second base material 402' needs to transmit the infrared laser. The material used for the second base material is preferably a resin having a composition that is identical or similar to that of the first base material. For example, when polypropylene is used as the first base material, a homopolypropylene or a random copolymer of polypropylene and polyethylene is preferred as the second base material. In general, the resins having an identical or similar composition easily bond with each other. Moreover, the resins having an identical or similar composition usually exhibit small difference in melting temperature. As a result, the effects of laser welding can be improved.

It is preferable that the second base material 402' be a plate-like or film-like base material having a smooth surface on both sides, although the wells 102, the flow passages and the support portion 405 can be formed by the same methods as those employed for the first base material. If a plate-like or film-like base material is used, the first base material and the second base material can be pasted together with good adhesion without fusion irregularities caused by differences in the base material thickness and the like. In addition, if the second base material has a thickness within the range from 0.01 mm to 2 mm, and more preferably from 0.05 to 0.5 mm, the welding properties and strength of the second base material can be ensured. Furthermore, because the second base material comes into contact with a heat block, satisfactory thermal efficiency can be achieved if the thickness is within the above-mentioned range.

FIG. 12 is a cross sectional view of the sample analysis chip illustrated in FIG. 11B taken along the dashed line S. In order to fill all the wells with the injected liquid sample, the volume of the main flow passage connected with the injection port needs to be larger than the sum of the volume of the respective wells. However, when a reagent is fixed in the well, the amount of liquid sample charged into the well reduces due to this, and thus the volume of main flow passage may be reduced by the same extent.

In the sample analysis chip illustrated in FIG. 12, reagents are fixed in each well. By fixing different types of reagents in the respective wells, one type of specimen (sample) can be subjected to a plurality of treatments. Further, it may also be configured so that a portion of the reagent for actually carrying out the reaction is fixed in each well. The remaining reagent can be introduced together with the liquid sample.

The reagent 501 for reaction is fixed in the well 102 before pasting together the base materials. Different types of reagents can be used in each well. By fixing different types of reagents in the respective reaction wells, one type of specimen (sample) can be subjected to a plurality of treatments. Further, it may also be configured so that a portion of the reagent for actually carrying out the reaction is fixed in each well while the remaining reagent is introduced together with the liquid sample. As a result, the storage stability of the chip improves, and also different reactions can be carried out in the respective wells so that a plurality of examinations can be conducted at the same time.

In terms of the fixing method for the reagent 501, for example, a liquid reagent is added dropwise to the well portion of the first base material 401' using a pipette or the like, and the first base material is then centrifuged using a centrifugal apparatus at 2,000 to 3,000 rpm for about 5 minutes. As a result, an adequate amount of liquid reagent remains in a state where the liquid level is flat, and by drying this, the reagent can be fixed in the well.

Furthermore, a wax 502 may be added dropwise following fixation of the reagent in the well. More specifically, the wax is melted on a hot plate and added dropwise using a pipette so as to cover the dried reagent. At this time, the wax is solidified within a few seconds. The wax has a role in fixing the reagent in the recess portion of the well.

Next, in the sample analysis chip of the present invention, reagents are fixed in a pit of the well 102 in the first base material 401' side, followed by fusion of the first base material and the second base material by the infrared laser, thereby producing a sealed-type chip. Although there are no particular limitations on the infrared laser as long as it can melt the surface of the first base material, the wavelength of infrared rays is preferably from 800 to 1,200 nm since it is suited for laser welding. From a practical point of view, the output of laser welding machine is preferably at least 30 W. For example, since the laser machines with an output of 30 to 250 W are commercially available, these laser machines can be used without any particular problems. More specifically, by pasting together the first base material and the second base material, and scanning and irradiating the chip with a laser beam from the second base material side at a constant speed through the use of, for example, an infrared photodiode laser beam having a wavelength of about 808 nm, the first base material and the second base material are welded. The laser welding can be carried out efficiently by adjusting the laser output power and the scanning speed. The production process for the sample analysis chip can be completed by the steps described above.

Next, a sample analysis method using the sample analysis chip according to the respective embodiments of the present invention will be described.

The sample analysis chip of the present invention can be used, for example, for the detection and analysis of biochemical substances in the samples of DNA, proteins, or the like. Reagents are fixed in each well 102 and the liquid sample is delivered to each well. In this case, different types of reagents can be used in each well. Alternatively, the sample is fixed in each well and the liquid reagent is delivered to each well. In this case, different types of samples can be used in each well.

Next, with respect to the sample analysis chip of the present invention prepared by pasting together the first base material 401 and the second base material 402, a solution such as a reagent is first injected from the injection port 403 (107) into the main flow passage 103. At this stage, only the main flow passage is filled with the solution and the solution has not entered the side passage. This is due to the surface tension of the solution and an air pressure from the well side since there is no air hole in the well side. A sample analyzer used in the sample analysis method may include such a solution injecting means.

Next, a sample analyzer used in the sample analysis method includes a chip rotating mechanism for rotating the sample analysis chip. A known centrifugal apparatus can be used as the chip rotating mechanism. The sample analysis chip is installed in the sample analyzer, and the chip is rotated by the rotating mechanism with the vertical direction of the chip serving as the axis of ration at the central point of the chip. In terms of the rotation speed, a rotation speed is required for causing the centrifugal force applied to the solution to overcome the aforementioned air pressure and surface tension so that the solution flows into the well. Although depending on the chip form, a rotation speed of about 1,000 rpm or higher is preferred. If the rotation speed of the chip is less than 1,000 rpm, the solution does not flow into the well, and the amount of liquid may not become constant.

Following delivery of liquid samples, an oil which does not inhibit the reaction of samples and reagents may be delivered to each well by the same process. Liquid evaporation can be prevented during reactions due to the injection of oil. It is necessary to use an oil having a lower specific weight than the solution delivered beforehand. This is because the oil plays a role as a stopper for each well in the side passage side when a liquid is delivered through the centrifugal force by rotating the chip. Although there are no particular limitations on the type of oil so long as it does not inhibit the reaction of samples and reagents, mineral oil and silicon oil can be suitably used.

When the wax 502 is used for fixing reagents, the sample analyzer may include a heater constituted of a heating wire or the like, or a temperature controlling means using a Peltier device. By heating the chip at a temperature equal to or higher than the melting point for the wax, the wax can be melted, thereby mixing the reagent and the solution (sample) within the well. Moreover, this temperature controlling means can also be used, for example, for controlling reagent reactions such as PCR reactions.

Thereafter, it is possible to mix the reagents and samples in the well and to analyze the reaction state through techniques such as fluorescence detection. The sample analyzer includes a detecting and measuring means for conducting measurements at the position of the well in the upper base material side of the sample analysis chip. A predetermined well can be measured by rotating the chip through the rotating mechanism. In the sample analysis chip of the present invention, by making the upper side of the base material transparent, it is possible to perform an optical measurement from the outside of the chip.

By including a mechanism to act on the sample analysis chip in each step as described above, it is possible to configure a sample analyzer in which the space reduction and sample analysis are easy.

Next, an example of the sample analysis method of the present invention will be described.

Examples of genetic analyses include a detection of somatic mutations and a detection of germline mutations. Because the types of expressed proteins and the like differ depending on the differences in the genotypes, the action of drug-metabolizing enzymes may differ, for example. As a result, the optimum dose of a drug, the possibility of side effects, or the like varies between individuals. By taking advantage of these facts in medical practice and examining the "genotype" of each patient, personalized medicine can be put into practice.

Detection of SNPs

There are different base sequences that are specific to individuals in about 0.1% of the human genome, which is one of the germline mutations known as single nucleotide polymorphism (SNP). As a method to identify SNPs, for example, a PCR-Preferential Homoduplex Formation Assay (PCR-PHFA) method using fluorescence has been employed. The PCR-PHFA method is constituted of a PCR step for amplifying the detected mutation sites and a substitution reaction step for the competing strands using the amplified fragments and the corresponding probe. Mutations are detected by the difference in light emission of fluorescent reagents according to this method, and an accurate detection of SNPs can be carried out by using the sample analysis chip of the present invention since variations in the delivery of liquid to each well are minimal. In addition, the sample analysis chip of the present invention can also be employed in the same manner in methods, other than the above-mentioned method, for detecting SNPs such as an invader method (registered trademark), TaqMan PCR method or the like.

An example of analysis for the SNPs involved in the side effects caused by warfarin (i.e., an anticoagulant agent which is a drug used for treating heart disease and hypertension) by employing the present invention with the use of PCR-PHFA method is described below.

Sample nucleic acids obtained from blood or the like are purified to prepare a solution sample. The sample nucleic acids are amplified prior to the injection into the sample analysis chip of the present invention or after the injection and prior to the liquid delivery. SNPs within the VKORC1 and CYP2C9 genes are often discussed in terms of the detection of SNPs in connection with warfarin, and CYP2C9*2 and CYP2C9*3 are well known examples. Gene fragments from the specimen including these SNPs are amplified by multiplex PCR.

In the above-mentioned detection method, two wells are required for detection in order to identify one single SNP. Therefore, it is preferable to use a sample analysis chip in which 10 or more wells are formed for each specimen sample, and reagents for SNP detection in order to carry out the competing-strand substitution reaction are fixed in each well.

The sample containing nucleic acids amplified by the above-mentioned PCR is delivered to load each well. The temperature in each well is controlled, and mutations are detected by the difference in light emission of fluorescent reagents mixed with the aforementioned reagents. For one single SNP, it can be identified as homozygous if only one of the two wells showed a positive reaction and as heterozygous when two wells showed a positive reaction.

Detection of Mutations in K-ras Gene

Most of the mutations unique to epithelial cancer cells and the mutations that express resistance to molecular-targeted drugs are somatic mutations. While common mutations can be observed in any cells in the case of germline mutations (such as SNPs), in the case of somatic mutations, mutations can be found only in the mutated cells and no mutation can be observed in non-mutated cells (usually, in the form of normal cells).

In other words, when the sample contains only a portion of mutant cells while the majority being normal cells, a fraction of mutated genes present among the numerous normal genes needs to be detected. This is different from the detection of mutations in germ cells, making the detection of gene mutations in somatic cells difficult.

It has been shown that molecular-targeted drugs are ineffective in most patient groups when a mutation is present in the K-ras gene in cancer cells, and thus a detection of this gene with high precision at low cost through a simple and rapid process has been desired.

An example for the analysis of K-ras gene by the PCR-PHFA method is described below.

A reagent containing a probe nucleic acid is fixed in the well for detecting the above-mentioned gene mutations. For the detection of K-ras gene, since there are 13 types of mutations as well as the wild type, it is preferable to use the sample analysis chip of the present invention having at least 14 wells formed therein and to fix the corresponding reagents to the wells.

Cancer cells such as colon cancer cells are collected, and the sample nucleic acids are purified to prepare a solution sample. The sample nucleic acids are amplified prior to the injection into the sample analysis chip of the present invention or after the injection and prior to the liquid delivery.

The sample containing nucleic acids amplified by the above-mentioned PCR is delivered to load each well. The temperature in each well is controlled, and mutations can be detected by the difference in light emission of fluorescent reagents mixed with the aforementioned reagents.

EXAMPLES

Examples in the present invention are provided below. However the present invention is in no way limited by these examples.

Example 1

In Example 1, an example where the sample analysis chip of the present invention is used as a SNP analysis chip is shown.

A chip having a disc-like outer shape as shown in FIG. 2 and concentrically including wave-like main flow passages 103, side passages 105 having a communication port at main flow passage valley portions 103b, and wells 102 at the end of side passages was formed as a SNP chip base material by injection molding using a polypropylene resin. 23 wells and side passages are each formed in this base material (polypropylene base material). In addition, it was designed so that the area of main flow passage was changed periodically and that the volume of main flow passage between the neighboring main flow passage peak portions 103a was 12 μl.

An aluminum sheet base material coated with a polypropylene resin as a resin coating layer was used as the second base material to be pasted together with the above-mentioned polypropylene base material. A resin coating layer having a thickness of 0.07 mm was used. The resin coating layer has a melting point of about 120 degrees, and is coated on the aluminum base material so as to melt when heat is applied to the aluminum side.

Further, it is configured so that an anchor layer containing carbon kneaded therein is provided between the aluminum layer and the resin coating layer is melted even with the heat generated by the irradiation of laser beam.

A probe reagent for invader reaction and enzymes such as DNA polymerase and Cleavase were added dropwise using a pipette to the well on the polypropylene base material, and were dried and fixed therein.

By superposing the polypropylene base material and the aluminum base material and heating the aluminum base material side at a temperature of 130 degrees or higher, the resin coating layer was melted, thereby fusing the polypropylene base material and the aluminum base material.

A solution sample prepared by adding the purified genomic DNA to a buffer solution was delivered to the chip prepared by the above-mentioned step using a pipette to load the main flow passage 103. At this stage, the sample had not entered the well and the side passage.

Note that each of the above-mentioned reagents was used in a quantity described in Table 1 shown below.

TABLE 1

| Type of reagents | Quantity/well (μl) |
| --- | --- |
| Probe reagent for invader reaction | 1.28 |
| DNA polymerase, Cleavase | 1.41 |
| Buffer solution (MgCl$_2$, NaCl) Purified genome (5 ng/μl) | 12 in total |
| Mineral oil | 12 |

Following liquid supply, 11 μl of sample was supplied to each well when the chip was rotated at 5,000 rpm with the chip center serving as an axis. As a means to provide centrifugal force to the chip, a simple centrifugal apparatus was made using a small desktop centrifuge used for the separation of reagents in the chemical and biological reactions or the like. This centrifugal apparatus was used. The rotational frequency during centrifugation was measured and adjusted using a rotational frequency measuring instrument.

It should be noted that in terms of the rotation direction of chip during centrifugation, regardless of the rotation direction with respect to the inclined direction of side passage, it was confirmed that variations in the liquid delivery to the well were not affected, although the liquid behavior inside the chip is affected during the increase of rotational frequency.

Subsequently, when mineral oil which did not inhibit the reaction was supplied by the same technique, the sample filled the wells, the remaining solution filled about a half of the side passages, and the oil filled the rest of the side passages and 80% of the flow passage valley portions.

Note that the probe for invader reaction was fixed in 22 wells as a reaction reagent in the present example. In addition, in order to assess the success and failure of the reaction results, one place was designated for the negative control to confirm the presence of contamination, and the reaction test was conducted on one single chip.

The genomic DNA in the sample was amplified by the PCR reaction. The sample analysis chip in a state where this reaction vessel was made independent by the oil was subjected to a PCR reaction consisted of 35 cycles of 95° C. and 68° C., thereby amplifying the genomic DNA in the sample. Subsequently, by controlling the temperature to 63° C. for 30 min, fluorescence is emitted due to the enzymatic reaction within the well.

Further, since the polypropylene base material side of the chip is transparent at this time, the fluorescence detection was conducted from the outside through the polypropylene base material. In the present example, the above fluorescence reaction was measured using a fluorescence detector in which a photomultiplier and optical fibers were combined.

Figure 13:
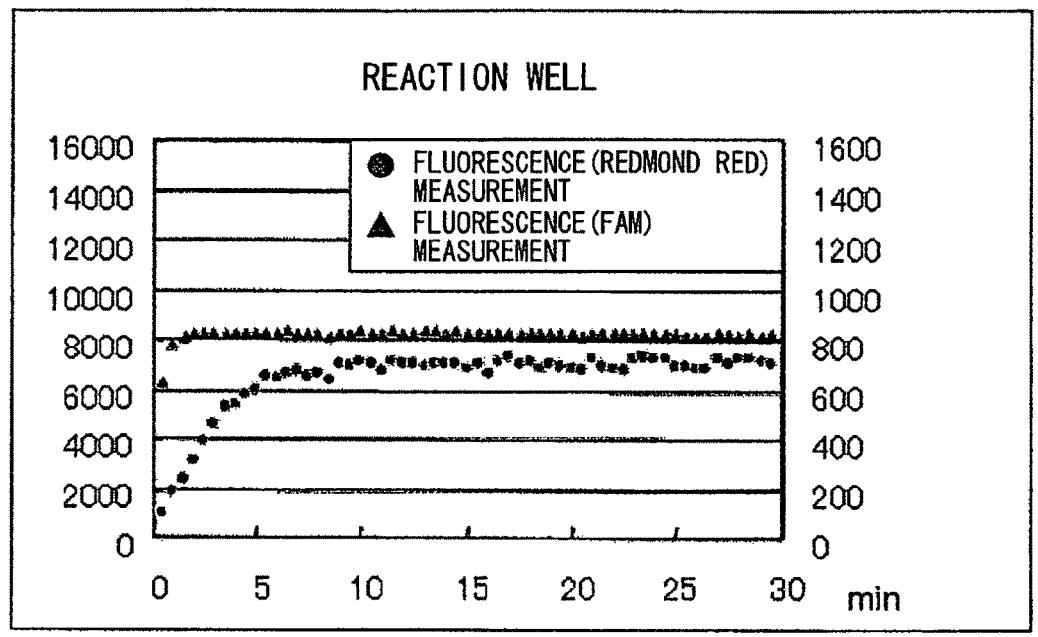
FIG. 13 is a graph which shows detection and measurement results in Example 1.
Figure 14:
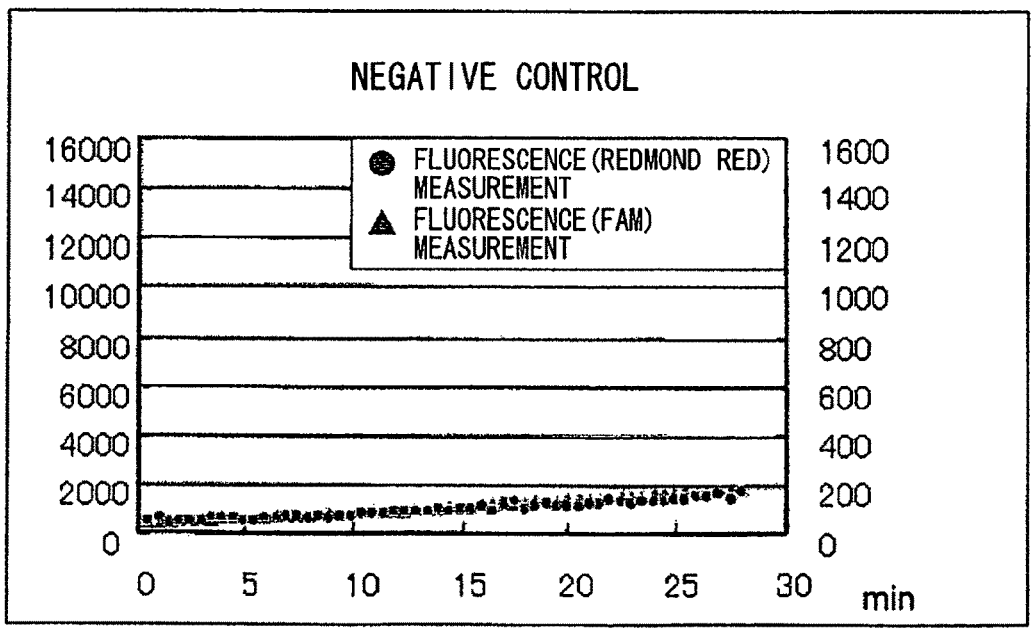
FIG. 14 is a graph which shows measurement results for a negative control.

FIG. 13 and FIG. 14 are graphs showing the analytical results for SNPs through the fluorescence reaction detected in the present example. The vertical axis in each graph shows the intensity of detected light, which indicates the intensity of fluorescence. The horizontal axis indicates time.

FIG. 13 shows a result from one single well where the reaction was conducted. It was confirmed that fluorescence reaction occurred due to the reagents mixed therein within a prescribed time.

FIG. 14 shows a result from the well where the reagents were not fixed in advance. Therefore, no fluorescence reaction was detected. These results confirm the absence of contamination from both of the neighboring wells.

Figure 15:
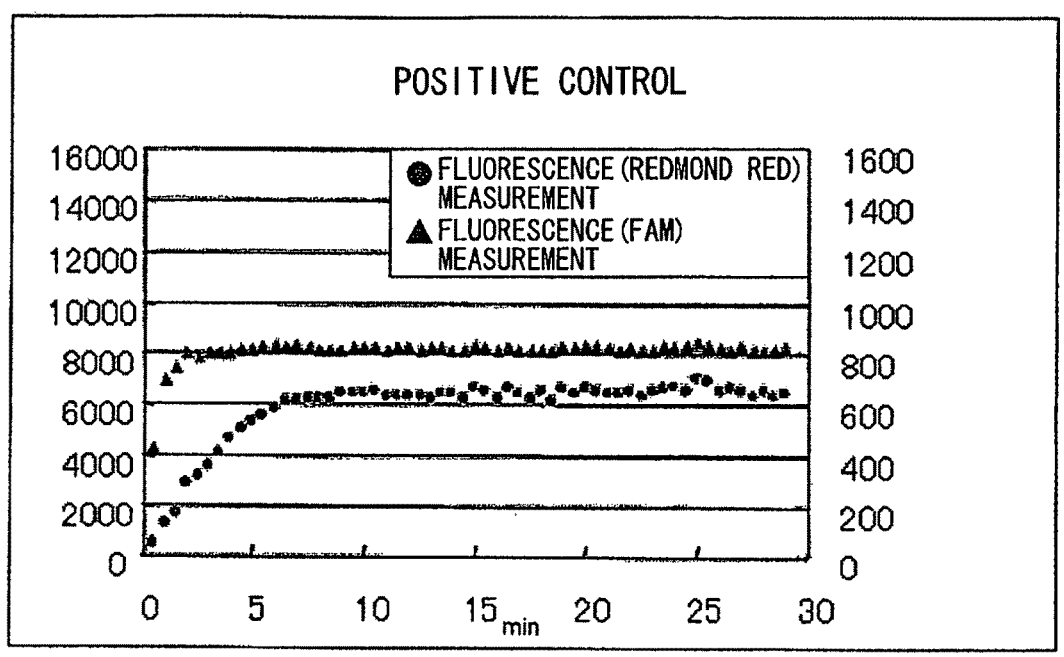
FIG. 15 is a graph which shows measurement results for a positive control.

Further, FIG. 15 shows detection data (positive control) obtained through a general technique by mixing the reagents and the sample at the optimum quantity ratio using a polypropylene tube. When comparing FIG. 13 and FIG. 15, since the reaction within the chip by the present example shown in FIG. 13 coincides with the reaction illustrated in FIG. 15, it was verified that the reaction in the present example was carried out at the optimum quantity ratio. As a result, it is clear that a desired amount of sample was delivered.

As described in the present Example 1, by selecting the base materials to be pasted together from the materials suitable for the reaction, it became possible to carry out the reaction step more simply and also efficiently within a short space of time.

Example 2

The sample analysis chip of the present invention having flow passages with a different shape was examined as Example 2.

In the present example, the sample analysis chip with a shape shown in FIG. 3 was prepared. The chip was prepared in Example 1 by injection molding of a polypropylene resin exhibiting a high level of chemical resistance in order to prevent mixing of inhibitors for the biochemical reactions. However, in order to examine the effects of the shape of flow passages, an acrylic resin was subjected to a mechanical cutting process to form the flow passages using endmills with diameters from φ 6 mm to φ 0.4 mm in this example.

By employing the sample analysis chip (chip 1) used in Example 1 with a shape illustrated in FIG. 2 and the sample analysis chip (chip 2) described above with a shape illustrated in FIG. 3, pure water stained with a bromophenol blue dye was supplied to the main flow passage, and the disc-shaped chip was rotated at 5,000 rpm with the chip center serving as an axis as in Example 1, and variations were measured in 10 trials. Note that in both sample analysis chips, under the assumption that a liquid is supplied equally to each well, the amount of liquid is 12 μl.

In the chip 1, the minimum value was 9.5 μl and the maximum value was 14.0 μl for the amount of supplied liquid. On the other hand, in the chip 2, the minimum value was 11.0 μl and the maximum value was 12.5 μl, indicating that variations in the amount of supplied liquid can be greatly suppressed even further.

Example 3

A chip having a disc-like outer shape as shown in FIG. 7 and concentrically including wave-like main flow passages 103, side passages 105 having a communication port at main flow passage valley portions 103b, wells 102 at the end of side passages, well branch flow passage 105a branched from the side passages, waste solution chamber branch flow passage 104a and the waste solution chamber 105b was formed as a first base material 401 for the sample analysis chip according to the present invention in Example 3 by injection molding using a polypropylene resin. 23 wells and side passages are each formed in this base material (polypropylene base material). It was designed so that the area of main flow passage was changed periodically and that the volume of valley portions 103b between the peaks of the main flow passage was 15 μA, and also that the volume of the well branch flow passage was 2 μl, the internal volume of wells was 11 μl, and the volume of waste solution chamber was 5 μl.

An aluminum sheet base material coated with a polypropylene resin as a resin coating layer was used as the second base material 402 to be pasted together with the above-mentioned polypropylene base material. A resin coating layer having a thickness of 0.07 mm was used. The resin coating layer has a melting point of about 120 degrees, and is coated on the aluminum base material so as to melt when heat is applied to the aluminum side.

Further, it is configured so that an anchor layer containing carbon kneaded therein is provided between the aluminum layer and the resin coating layer is melted even with the heat generated by the irradiation of laser beam.

A probe reagent for invader reaction and enzymes such as DNA polymerase and Cleavase were added dropwise using a pipette to the well on the polypropylene base material, and were dried and fixed therein.

By superposing the polypropylene base material and the aluminum base material and heating the aluminum base material side at a temperature of 130 degrees or higher, the resin coating layer was melted, thereby fusing the polypropylene base material and the aluminum base material.

A solution sample prepared by adding the purified genomic DNA to a buffer solution was supplied to the chip prepared by the above-mentioned step using a pipette to load the main flow passage 103. At this stage, the sample had not entered the well and the side passage.

Note that each of the above-mentioned reagents was used so that the quantity thereof was the same as those described in Table 1 in Example 1.

Following liquid supply, the respective wells and the well branch flow passages were filled with the solution, and 0.5 μl to 3 μl of solution was stored in the waste solution chamber when the chip was rotated at 5,000 rpm with the chip center serving as an axis. 11 μl of sample was supplied to each well. As a means to provide centrifugal force to the chip, a simple centrifugal apparatus was made using a small desktop centrifuge used for the separation of reagents in the chemical and biological reactions or the like. This centrifugal apparatus was used. The rotational frequency during centrifugation was measured and adjusted using a rotational frequency measuring instrument.

It should be noted that in terms of the rotation direction of chip during centrifugation, regardless of the rotation direction with respect to the inclined direction of side passage, it was confirmed that variations in the liquid delivery to the well were not affected, although the liquid behavior inside the chip is affected during the increase of rotational frequency.

Subsequently, when the mineral oil described in the reagent table (Table 1) which did not inhibit the reaction was supplied by the same technique, the sample filled the wells, the remaining solution filled about a half of the side passages, and the mineral oil completely filled the well branch flow passage, the waste solution chamber branch flow passage and the side passages, and also a portion of the main flow passages.

Note that the probe for invader reaction was fixed in 22 wells as a reaction reagent in the present example. In addition, in order to assess the success and failure of the reaction results, one place was designated for the negative control to confirm the presence of contamination, and the reaction test was conducted on one single chip.

The genomic DNA in the sample was amplified by the PCR reaction. The sample analysis chip in a state where this reaction vessel is made independent by the oil was subjected to a PCR reaction consisted of 35 cycles of 95° C. and 68° C., thereby amplifying the genomic DNA in the sample. Subsequently, by controlling the temperature to 63° C. for 30 min, fluorescence is emitted due to the enzymatic reaction within the well.

Further, since the polypropylene base material side of the chip is transparent at this time, the fluorescence detection was conducted from the outside through the polypropylene base material. In the present example, the above fluorescence reaction was measured using a fluorescence detector in which a photomultiplier and optical fibers were combined.

As a result of the measurement, because of the reagents delivered to each well, it was confirmed, as in Example 1, that fluorescence reaction occurred due to the reagents mixed therein within a prescribed time. Thus, the same results as the detection data obtained through a general technique by mixing the reagents and the sample at the optimum quantity ratio were obtained. Further, in the well for the negative control, no fluorescence reaction was detected. These results confirm the absence of contamination from both of the neighboring wells.

Example 4

As an example for the sample analysis chip of the present invention, the sample analysis chip illustrated in FIG. 11(B) and FIG. 3 was prepared. A polypropylene resin was used as a first base material 401', which was processed by injection molding. The side passages 105 had a width of about 1 mm, and the wells 102 had a trapezoidal shape with a flat upper portion while the well bottom had a diameter of about 3 mm and a volume of about 7 μl.

Since polypropylene does not exhibit absorption in the infrared region, it is necessary to add an infrared absorbing agent to a propylene resin. In the present example, 0.01 parts by weight of Lumogen (registered trademark) IR765 manufactured by BASF was added and mixed in advance as an infrared absorbing agent relative to 100 parts by weight of propylene resin to prepare a propylene resin pellet containing an infrared absorbing agent. The first base material for the above-mentioned sample analysis chip was prepared by injection molding using this pellet.

Further, a propylene film having a thickness of about 0.15 mm was used as the second base material 402'.

A probe reagent for invader reaction and enzymes such as DNA polymerase and Cleavase were added dropwise using a pipette to the well on the first base material 401', and were dried and fixed therein.

By superposing the first base material 401' and the second base material 402', and scanning and irradiating the chip with a laser beam from the second base material side at a constant speed through the use of an infrared photodiode laser beam having a wavelength of 808 nm and an output of 140 W, the first base material and the second base material were welded.

A solution sample prepared by adding the purified genomic DNA to a buffer solution was supplied to the chip prepared by the above-mentioned step using a pipette to load the main flow passage 103. At this stage, the sample had not entered the well and the side passage.

Note that each of the above-mentioned reagents was used so that the quantity thereof was the same as those described in Table 1 in Example 1.

Following liquid supply, 11 µl of sample was supplied to each well when the chip was rotated at 5,000 rpm with the chip center serving as an axis. As a means to provide centrifugal force to the chip, a simple centrifugal apparatus was made using a small desktop centrifuge used for the separation of reagents in the chemical and biological reactions or the like. This centrifugal apparatus was used. The rotational frequency during centrifugation was measured and adjusted using a rotational frequency measuring instrument.

Subsequently, when the mineral oil described in the reagent table (Table 1) which did not inhibit the reaction was supplied by the same technique, the sample filled the wells, and the remaining solution filled about a half of the side passages.

Note that the probe for invader reaction was fixed in 22 wells as a reaction reagent in the present example. In addition, in order to assess the success and failure of the reaction results, one place was designated for the negative control to confirm the presence of contamination, and the reaction test was conducted on one single chip.

The genomic DNA in the sample was amplified by the PCR reaction. The sample analysis chip in a state where this reaction vessel is made independent by the oil was subjected to a PCR reaction consisted of 35 cycles of 95° C. and 68° C., thereby amplifying the genomic DNA in the sample. Subsequently, by controlling the temperature to 63° C. for 30 min, fluorescence is emitted due to the enzymatic reaction within the well.

Further, at this time, the fluorescence detection was conducted from the outside in the first base material 401' side of the chip. In the present example, the above fluorescence reaction was measured using a fluorescence detector in which a photomultiplier and optical fibers were combined.

As a result of the measurement, because of the reagents delivered to each well, it was confirmed, as in Example 1, that fluorescence reaction occurred due to the reagents mixed therein within a prescribed time. Thus, the same results as the detection data obtained through a general technique by mixing the reagents and the sample at the optimum quantity ratio were obtained. Further, in the well for the negative control, no fluorescence reaction was detected. These results confirm the absence of contamination from both of the neighboring wells.

[Industrial Applicability]

The reaction chip of the present invention can be used, for example, for the detection and analysis of biochemical substances in the samples of nucleic acids or the like. Especially, because mutations in the SNPs can be detected, it can be applied to a technique for detecting genes related to cancer and the like, or gene mutations in germ cells and somatic cells. In addition, it can be used as a vessel for mixing a plurality of solutions or as a reaction vessel.

[Reference Signs List]

101: Base material; 102: Well; 103: Main flow passage; 103a: Main flow passage peak portion; 103b: Main flow passage valley portion; 104: Waste solution portion; 104a: Waste solution chamber branch flow passage; 104b: Waste solution chamber; 105a: Well branch flow passage; 105: Side passage; 107: INLET/OUTLET; 401: First base material; 401': First base material (optically transparent resin); 402: Second base material; 402': Second base material (infrared transmitting resin); 403: INLET/OUTLET (through hole); 405: Support portion; 501: Fixed reagents; 502: Wax

The invention claimed is:

1. A sample analysis chip comprising, on a base material:
a plurality of wells;
a flow passage leading to the respective wells; and
an injection port to inject a solution into the flow passage, and to deliver the solution to the wells by rotating the base material, wherein:
the flow passage includes a main flow passage which supplies liquid to the wells,
the main flow passage is provided closer to a rotation center side than to the wells; and
the main flow passage has the injection port at a first end, an exit at a second end, and has a plurality of peaks between the first and second ends, so that each of the peaks is between neighboring wells in a direction of rotation center.

2. The sample analysis chip according to claim 1, wherein the well and the main flow passage are connected in a valley portion between peaks of the main flow passage.

3. The sample analysis chip according to claim 1, wherein a passage width of the main flow passage is relatively small in a peak portion and large in a valley portion.

4. The sample analysis chip according to claim 1,
wherein the base material has a disc shape and the wells are arranged concentrically to the base material.

5. The sample analysis chip according to claim 1, wherein the flow passage further comprises a plurality of side passages that connect the main flow passage to the respective wells.

6. The sample analysis chip according to claim 5, wherein each of the side passages is formed so as to be inclined with respect to the direction of rotation center.

7. The sample analysis chip according to claim 1,
wherein the main flow passage is formed so as to be inclined with respect to the direction of rotation center.

8. The sample analysis chip according to claim 1, wherein the flow passage further comprises:
a plurality of side passages that connect the main flow passage to the respective wells; and
a waste solution portion provided in each of the side passages to store a residual solution.

9. The sample analysis chip according to claim 8,
wherein the waste solution portion includes a waste solution chamber to store a waste solution, and a waste solution chamber branch flow passage that is branched from the side passage and connected to the waste solution chamber.

10. The sample analysis chip according to claim 8,
wherein each of the side passages is formed so as to be inclined with respect to the direction of rotation center, and
the waste solution portion is provided on an inner side of the side passage with respect to the direction of rotation center.

11. The sample analysis chip according to claim 9,
wherein the branch flow passage connected to the well has a lower pressure loss during a liquid supply than the branch flow passage connected to the waste solution chamber.

12. The sample analysis chip according to claim 11, wherein an inner surface of the waste solution chamber branch flow passage is subjected to a water repellency treatment.

13. The sample analysis chip described in claim 11, wherein an inner surface of the branch flow passage connected to the well is subjected to a hydrophilic treatment.

14. The sample analysis chip according to claim 1,
wherein the sample analysis chip includes a first base material having the well and the flow passage formed therein and a second base material pasted together with the first base material.

15. The sample analysis chip according to claim 14, wherein either one of the base materials is formed of an optically transparent material.

16. The sample analysis chip according to claim 15,
wherein the first base material is an optically transparent resin material and the second base material is a metallic material.

17. The sample analysis chip according to claim 15,
wherein the first base material is formed of a resin that is optically transparent with respect to visible light and light absorptive with respect to infrared rays, and
the second base material is a plate-shaped or film-shaped material that transmits infrared rays having a wavelength of at least 800 nm.

18. The sample analysis chip according to claim 17,
wherein the first base material is any one of the resin base materials among polypropylene resins, polycarbonate resins and acrylic resins.

19. The sample analysis chip according to claim 17,
wherein the first base material includes an infrared absorbing agent having an absorption peak within a wavelength region of at least 800 nm.

20. A method of producing the sample analysis chip described in claim 17 further comprising:
irradiating an infrared laser from the second base material side; and
melting and bonding the first base material and the second base material, thereby pasting them together.

21. The method of producing a sample analysis chip according to claim 20, wherein the infrared laser has a wavelength within a range from 800 to 1,200 nm.

22. The method of producing a sample analysis chip according to claim 20, further comprising fixing a reagent in the well before pasting together the first base material and the second base material during production of the sample analysis chip.

23. The sample analysis chip according to claim 1,
wherein the second base material is any one of the resin base materials among polypropylene resins, polycarbonate resins and acrylic resins.

24. The sample analysis chip according to claim 1, wherein a thickness of the second base material is within a range from 0.05 to 0.5 mm.

25. The sample analysis chip according to claim 1, wherein a support portion for rotating a sample analysis chip is provided in the first base material.

26. A sample analyzer comprising:
a device for installing and rotating the sample analysis chip described in claim 1; and
a detecting and measuring device to detect a reaction in the well.

27. A sample analysis method further comprising:
injecting a solution in the main flow passage of the sample analysis chip described in claim 1; and
rotating the sample analysis chip and thereby delivering the solution to the respective wells.

28. The sample analysis method according to claim 27, further comprising
delivering a mineral oil to the respective wells following the delivering the solution to the respective wells.

29. A genetic analysis method using the sample analysis method described in claim 27.

30. A sample analysis chip comprising, on a base material:
a plurality of wells;
a flow passage leading to the respective wells; and
an injection port to inject a solution into the flow passage, and to deliver the solution to the wells by rotating the base material;
wherein the flow passage includes:
a main flow passage which supplies liquid to the respective wells, the main flow passage being provided closer to a rotation center side than to the wells, and being formed so as to have one peak between neighboring wells in a direction of a rotation center;
a plurality of side passages that connect the main flow passage to the respective wells; and
a waste solution portion provided in the side passages to store a residual solution,
wherein the waste solution portion includes a waste solution chamber to store a waste solution, and a waste solution chamber branch flow passage that is branched from the side passage and connected to the waste solution chamber,
wherein the branch flow passage connected to the well has a lower pressure loss during a liquid supply than the branch flow passage connected to the waste solution chamber, and
wherein a cross sectional area of the branch flow passage connected to the well is larger than a cross sectional area of the waste solution chamber branch flow passage.

31. A sample analysis chip comprising on a base material:
a plurality of wells;
a flow passage leading to the respective wells; and
an injection port to inject a solution into the flow passage, and to deliver the solution to the wells by rotating the base material;
wherein the flow passage includes;
a main flow passage which supplies liquid to the respective wells, the main flow passage being provided closer to a rotation center side than to the wells, and being formed so as to have one peak between neighboring wells in a direction of a rotation center,
a plurality of side passages that connect the main flow passage to the respective wells; and a waste solution portion provided in the side passages to store a residual solution, wherein the waste solution portion includes a waste solution chamber to store a waste solution, and a waste solution chamber branch flow passage that is branched from the side passage and connected to the waste solution chamber, wherein the branch flow passage connected to the well has a lower pressure loss during a liquid supply than the branch flow passage connected to the waste solution chamber, and wherein the branch flow passage connected to the well has a lower surface roughness than the waste solution chamber branch flow passage.

\* \* \* \* \*

UNITED STATES PATENT AND TRADEMARK OFFICE
CERTIFICATE OF CORRECTION

| | |
|---|---|
| PATENT NO. | : 8,546,129 B2 |
| APPLICATION NO. | : 13/138756 |
| DATED | : October 1, 2013 |
| INVENTOR(S) | : Tomoyuki Ozawa et al. |

Page 1 of 1

It is certified that error appears in the above-identified patent and that said Letters Patent is hereby corrected as shown below:

On the Title Page, In Column 2 Item (57) (Abstract), Line 9, Delete "well;" and insert -- well, --, therefor.

Signed and Sealed this
First Day of April, 2014

Michelle K. Lee
*Deputy Director of the United States Patent and Trademark Office*